US007422585B1

(12) United States Patent
Eggers et al.

(10) Patent No.: US 7,422,585 B1
(45) Date of Patent: *Sep. 9, 2008

(54) SYSTEM FOR ELECTROSURGICAL MYOCARDIAL REVASCULARIZATION

(75) Inventors: Philip E. Eggers, Dublin, OH (US); Hira V. Thapliyal, Los Altos, CA (US)

(73) Assignee: ArthroCare Corporation, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/347,390

(22) Filed: Jul. 6, 1999

Related U.S. Application Data

(60) Division of application No. 09/054,660, filed on Apr. 3, 1998, now abandoned, which is a continuation of application No. 08/753,227, filed on Nov. 22, 1996, now Pat. No. 5,873,855, which is a continuation-in-part of application No. 08/562,331, filed on Nov. 22, 1995, now Pat. No. 5,683,366, which is a continuation-in-part of application No. 08/485,219, filed on Jun. 7, 1995, now Pat. No. 5,697,281, which is a continuation-in-part of application No. PCT/US94/05168, filed on May 10, 1994, which is a continuation-in-part of application No. 08/059,681, filed on May 10, 1993, now abandoned, which is a continuation-in-part of application No. 07/958,977, filed on Oct. 9, 1992, now Pat. No. 5,366,443, which is a continuation-in-part of application No. 07/817,575, filed on Jan. 7, 1992, now abandoned.

(51) Int. Cl.
*A61N 1/00* (2006.01)

(52) U.S. Cl. ............................. 606/41; 606/48; 607/101; 607/122

(58) Field of Classification Search ................ 606/7, 606/10–12, 32–34, 41, 42, 48–50; 607/101, 607/102, 122
See application file for complete search history.

(56) References Cited

U.S. PATENT DOCUMENTS 2,050,904 A 8/1936 Trice ..................... 128/303

(Continued)

FOREIGN PATENT DOCUMENTS

CA 2067412 9/2004

(Continued)

OTHER PUBLICATIONS

Rand et al. (1985) *J. Arthro. Surg.* 1:242-246. Effect of Electrocautery on Fresh Human Articular Cartilage.

(Continued)

*Primary Examiner*—Michael Peffley
(74) *Attorney, Agent, or Firm*—Brian E. Szymczak

(57) ABSTRACT

A method for transmyocardial revascularization of the heart of a patient includes positioning an active electrode surface in close proximity to a target site on the wall of a patient's heart, and applying high frequency voltage between the active voltage surface and a return electrode to ablate tissue at the heart wall. The high frequency voltage ablates, i.e. volumetrically removes the heart tissue, and the electrode surface is axially translated into the space vacated by the removed tissue to bore a channel through the heart tissue. The active electrode surface may be introduced into the thoracic cavity and placed adjacent the epicardium to form an inward channel toward the ventricular cavity, or it may be delivered into the ventricular cavity of the heart and positioned adjacent the endocardium to form a channel extending outward towards the epicardium. In either case, the channels formed through the myocardium promote direct communication between blood within the ventricular cavity and that of existing myocardial vasculature to increase blood flow to the heart tissue.

31 Claims, 21 Drawing Sheets

U.S. PATENT DOCUMENTS

| | | | |
|---|---|---|---|
| 2,056,377 A | 10/1936 | Wappler | 125/303 |
| 3,460,539 A | 8/1969 | Anhalt | 128/304 |
| 3,633,425 A | 1/1972 | Sanford | 73/356 |
| 3,769,984 A | 11/1973 | Muench | 128/404 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,011,872 A | 3/1977 | Komiya | 606/47 |
| 4,033,351 A | 7/1977 | Hetzel | 128/303 |
| 4,038,519 A | 7/1977 | Faucras | 392/472 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,590,934 A | 5/1986 | Malis et al. | 128/303 |
| 4,593,691 A | 6/1986 | Lindstrom et al. | 128/303 |
| 4,641,649 A | 2/1987 | Walinsky | 128/303 |
| 4,658,817 A | 4/1987 | Hardy | 128/303 |
| 4,660,571 A | 4/1987 | Hess et al. | 128/784 |
| 4,674,499 A | 6/1987 | Pao | 128/303 |
| 4,682,596 A | 7/1987 | Bales et al. | 604/22 |
| 4,699,157 A | 10/1987 | Shonk | 607/122 |
| 4,706,667 A | 11/1987 | Roos | 128/303 |
| 4,709,698 A | 12/1987 | Johnston et al. | 128/303 |
| 4,727,874 A | 3/1988 | Bowers et al. | 128/303 |
| 4,753,223 A | 6/1988 | Bremer | 600/140 |
| 4,754,752 A | 7/1988 | Ginsburg et al. | 606/27 |
| 4,765,331 A | 8/1988 | Petruzzi et al. | 128/303 |
| 4,785,815 A | 11/1988 | Cohen | 128/642 |
| 4,785,823 A | 11/1988 | Eggers et al. | 128/692 |
| 4,796,622 A | 1/1989 | Lu et al. | 606/28 |
| 4,805,616 A | 2/1989 | Pao | 128/303 |
| 4,823,791 A | 4/1989 | D'Amelio | 128/303 |
| 4,832,048 A | 5/1989 | Cohen | 128/786 |
| 4,857,046 A | 8/1989 | Stevens et al. | 604/22 |
| 4,860,752 A | 8/1989 | Turner | 607/102 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 128/401 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,000,751 A | 3/1991 | Schroder et al. | 606/4 |
| 5,007,908 A | 4/1991 | Rydell | 606/47 |
| 5,009,656 A | 4/1991 | Reimels | 128/303 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,078,684 A | 1/1992 | Yasuda | 604/95 |
| 5,078,717 A | 1/1992 | Parins et al. | 606/48 |
| 5,078,736 A | 1/1992 | Behl | 623/1 |
| 5,080,660 A | 1/1992 | Buelna | 606/45 |
| 5,083,535 A | 1/1992 | Deschler et al. | 123/192.2 |
| 5,083,565 A | 1/1992 | Parins | 128/642 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,093,877 A | 3/1992 | Aita et al. | 385/34 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,104,391 A | 4/1992 | Ingle et al. | 606/11 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,114,402 A | 5/1992 | McCoy | 604/95.05 |
| 5,122,138 A | 6/1992 | Manwaring | 606/46 |
| 5,125,924 A * | 6/1992 | Rudko | 606/12 |
| 5,125,926 A | 6/1992 | Rudko et al. | 606/19 |
| 5,125,928 A | 6/1992 | Parins et al. | 606/48 |
| 5,156,151 A | 10/1992 | Imran | 128/642 |
| 5,163,938 A | 11/1992 | Kambara et al. | 606/47 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,188,635 A | 2/1993 | Radtke | 606/14 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,200,604 A | 4/1993 | Rudko et al. | 250/205 |
| 5,201,757 A | 4/1993 | Heyn et al. | 606/198 |
| 5,207,675 A | 5/1993 | Canady | 606/40 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,234,457 A | 8/1993 | Andersen | 606/198 |
| 5,242,399 A | 9/1993 | Lau et al. | 604/104 |
| 5,242,441 A | 9/1993 | Avitall | 606/41 |
| 5,246,438 A | 9/1993 | Langberg | 606/33 |
| 5,261,410 A | 11/1993 | Alfano et al. | 128/664 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,279,299 A | 1/1994 | Imran | 128/642 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,282,824 A | 2/1994 | Gianturco | 623/1.13 |
| 5,287,861 A | 2/1994 | Wilk | 128/898 |
| 5,290,273 A | 3/1994 | Tan | 606/9 |
| 5,290,282 A | 3/1994 | Casscells | 606/29 |
| 5,293,868 A | 3/1994 | Nardella | 128/642 |
| 5,300,069 A | 4/1994 | Hunsberger et al. | 606/37 |
| 5,304,170 A | 4/1994 | Green | 606/9 |
| 5,306,238 A | 4/1994 | Fleenor | 606/42 |
| 5,312,395 A | 5/1994 | Tan et al. | 606/9 |
| 5,312,400 A | 5/1994 | Bales et al. | 606/41 |
| 5,314,406 A | 5/1994 | Arias et al. | 604/21 |
| 5,318,525 A | 6/1994 | West et al. | 604/95 |
| 5,324,254 A | 6/1994 | Phillips | 604/21 |
| 5,330,470 A | 7/1994 | Hagen | 606/42 |
| 5,330,496 A | 7/1994 | Alferness | 606/171 |
| 5,334,140 A | 8/1994 | Philips | 604/35 |
| 5,334,190 A | 8/1994 | Seiler | 606/5 |
| 5,334,193 A * | 8/1994 | Nardella | 606/41 |
| 5,335,668 A | 8/1994 | Nardella | 128/734 |
| 5,336,217 A | 8/1994 | Buys et al. | 606/9 |

| Patent No. | Date | Inventor | Class |
|---|---|---|---|
| 5,342,357 A | 8/1994 | Nardella | 606/40 |
| 5,348,553 A | 9/1994 | Whitney | 606/41 |
| 5,348,554 A | 9/1994 | Imran et al. | 606/41 |
| 5,366,443 A | 11/1994 | Eggers et al. | 604/114 |
| 5,370,642 A | 12/1994 | Keller | 606/9 |
| 5,370,644 A | 12/1994 | Langberg | 606/33 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita et al. | 606/7 |
| 5,382,261 A | 1/1995 | Palmaz | 606/158 |
| 5,383,876 A | 1/1995 | Nardella | 606/49 |
| 5,383,917 A | 1/1995 | Desai et al. | 607/702 |
| 5,389,096 A * | 2/1995 | Aita et al. | 606/15 |
| 5,391,199 A | 2/1995 | Ben-Haim | 607/122 |
| 5,395,312 A | 3/1995 | Desai | 604/22 |
| 5,400,267 A | 3/1995 | Denen et al. | 702/59 |
| 5,400,428 A | 3/1995 | Grace | 385/115 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,421,955 A | 6/1995 | Lau et al. | 216/48 |
| 5,423,803 A | 6/1995 | Tankovich | 606/9 |
| 5,423,806 A | 6/1995 | Dale | 606/15 |
| 5,423,810 A | 6/1995 | Goble et al. | 606/40 |
| 5,423,882 A | 6/1995 | Jackman et al. | 607/122 |
| 5,425,355 A | 6/1995 | Kulick | 600/183 |
| 5,429,144 A | 7/1995 | Wilk | 128/898 |
| 5,429,604 A | 7/1995 | Hammersmark et al. | 604/95 |
| 5,431,649 A * | 7/1995 | Mulier et al. | 606/41 |
| 5,433,708 A | 7/1995 | Nichols et al. | 604/113 |
| 5,436,566 A | 7/1995 | Thompson et al. | 324/713 |
| 5,437,658 A | 8/1995 | Muller et al. | 606/5 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,445,634 A | 8/1995 | Keller | 606/9 |
| 5,451,224 A | 9/1995 | Goble et al. | 606/48 |
| 5,454,809 A | 10/1995 | Janssen | 606/41 |
| 5,456,680 A | 10/1995 | Taylor et al. | 606/2 |
| 5,462,544 A | 10/1995 | Saksena et al. | 606/15 |
| 5,464,404 A | 11/1995 | Abela et al. | 606/15 |
| 5,476,505 A | 12/1995 | Limon | 623/1 |
| 5,484,433 A | 1/1996 | Taylor et al. | 606/17 |
| 5,487,385 A | 1/1996 | Avitall | 128/642 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,500,012 A | 3/1996 | Brucker et al. | 607/122 |
| 5,505,725 A | 4/1996 | Samson | 606/7 |
| 5,507,771 A | 4/1996 | Gianturco | 606/198 |
| 5,514,128 A | 5/1996 | Hillsman et al. | 606/7 |
| 5,514,130 A | 5/1996 | Baker | 606/41 |
| 5,540,712 A | 7/1996 | Kleshinski et al. | 623/1 |
| 5,542,928 A | 8/1996 | Evans et al. | 604/113 |
| 5,545,161 A | 8/1996 | Imran | 606/41 |
| 5,545,211 A | 8/1996 | An et al. | 623/1 |
| 5,554,152 A | 9/1996 | Aita et al. | 606/7 |
| 5,556,397 A | 9/1996 | Long et al. | 606/48 |
| 5,567,890 A | 10/1996 | Lindberg et al. | 75/243 |
| 5,569,242 A | 10/1996 | Lax et al. | 606/42 |
| 5,571,100 A | 11/1996 | Goble et al. | 606/41 |
| 5,571,169 A | 11/1996 | Plaia et al. | 128/898 |
| 5,579,764 A | 12/1996 | Goldreyer | 607/122 |
| 5,584,872 A | 12/1996 | LaFontaine et al. | 607/116 |
| 5,591,159 A | 1/1997 | Taheri | 606/15 |
| 5,603,731 A | 2/1997 | Whitney | 607/121 |
| 5,607,421 A | 3/1997 | Jeevanandam et al. | 606/15 |
| 5,609,151 A | 3/1997 | Mulier et al. | 128/642 |
| 5,620,438 A | 4/1997 | Amplatz et al. | 606/10 |
| 5,626,576 A | 5/1997 | Janssen | 606/41 |
| 5,633,578 A | 5/1997 | Eggers et al. | 323/301 |
| 5,643,251 A | 7/1997 | Hillsman et al. | 606/7 |
| 5,643,255 A | 7/1997 | Organ | 606/41 |
| 5,647,869 A | 7/1997 | Goble | 606/37 |
| 5,662,124 A | 9/1997 | Wilk | 128/898 |
| 5,662,680 A | 9/1997 | Desai | 606/210 |
| 5,669,907 A | 9/1997 | Platt et al. | 606/48 |
| 5,672,170 A | 9/1997 | Cho et al. | 606/12 |
| 5,673,695 A | 10/1997 | McGee et al. | 128/642 |
| 5,676,693 A | 10/1997 | LaFontaine | 607/116 |
| 5,681,282 A | 10/1997 | Eggers et al. | 604/114 |
| 5,681,308 A | 10/1997 | Edwards et al. | 606/41 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,749,914 A | 5/1998 | Janssen | 607/116 |
| 5,766,153 A | 6/1998 | Eggers et al. | 604/114 |
| 5,766,164 A | 6/1998 | Mueller et al. | 606/15 |
| 5,766,192 A | 6/1998 | Zacca | 606/159 |
| 5,769,843 A | 6/1998 | Abela et al. | 606/10 |
| 5,775,338 A | 7/1998 | Hastings | 128/898 |
| 5,779,715 A | 7/1998 | Tu | 606/108 |
| 5,807,384 A | 9/1998 | Mueller | 606/7 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,817,013 A | 10/1998 | Ginn et al. | 600/114 |
| 5,823,955 A | 10/1998 | Kuck et al. | 600/374 |
| 5,824,005 A | 10/1998 | Motamedi et al. | 606/15 |
| 5,827,203 A | 10/1998 | Nita | 601/2 |
| 5,836,868 A | 11/1998 | Ressemann et al. | 606/159 |
| 5,836,875 A | 11/1998 | Webster, Jr. | 600/374 |
| 5,836,946 A | 11/1998 | Diaz et al. | 606/45 |
| 5,840,059 A | 11/1998 | March et al. | 604/509 |
| 5,843,019 A | 12/1998 | Eggers et al. | 604/22 |
| 5,860,951 A | 1/1999 | Eggers et al. | 604/49 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,133 A | 4/1999 | Murphy-Chutorian | 606/7 |
| 5,891,134 A | 4/1999 | Goble et al. | 606/27 |
| 5,891,140 A | 4/1999 | Ginn et al. | 606/48 |
| 5,893,848 A * | 4/1999 | Negus et al. | 606/41 |
| 5,893,885 A | 4/1999 | Webster, Jr. | 607/122 |
| 5,897,553 A | 4/1999 | Mulier | 606/41 |
| 5,902,272 A | 5/1999 | Eggers et al. | 604/114 |
| 5,902,289 A * | 5/1999 | Swartz et al. | 604/530 |
| 5,910,150 A | 6/1999 | Saadat | 606/159 |
| 5,913,853 A | 6/1999 | Loeb et al. | 606/15 |
| 5,944,715 A | 8/1999 | Goble et al. | 606/41 |
| 5,954,716 A | 9/1999 | Sharkey et al. | 606/32 |
| 5,980,515 A | 11/1999 | Tu | 606/41 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,032,674 A | 3/2000 | Eggers et al. | 128/898 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |

| Patent # | Date | Inventor | Class |
|---|---|---|---|
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,156,031 A * | 12/2000 | Aita et al. | 606/33 |
| 6,159,194 A | 12/2000 | Eggers et al. | 604/500 |
| 6,159,208 A | 12/2000 | Hovda et al. | 606/41 |
| 6,161,543 A | 12/2000 | Cox et al. | 128/898 |
| 6,168,593 B1 | 1/2001 | Sharkey et al. | 606/34 |
| 6,174,308 B1 | 1/2001 | Goble et al. | 606/41 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Eggers | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,517,498 B1 | 2/2003 | Burbank et al. | 600/564 |
| 6,530,922 B2 | 3/2003 | Cosman | 606/34 |
| 6,578,579 B2 | 6/2003 | Burnside | 128/897 |
| 6,582,423 B1 | 6/2003 | Thapliyal et al. | 606/32 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,915,806 B2 | 7/2005 | Pacek et al. | 128/898 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 2002/0029036 A1 | 3/2002 | Goble et al. | 606/38 |
| 2002/0095151 A1 | 7/2002 | Dahla et al. | 606/41 |
| 2003/0013986 A1 | 1/2003 | Saadat | 600/549 |
| 2003/0028189 A1 | 2/2003 | Woloszko et al. | 604/45 |
| 2003/0088245 A1 | 5/2003 | Woloszko et al. | 606/41 |
| 2003/0158545 A1 | 8/2003 | Hovda et al. | 606/32 |
| 2003/0171743 A1 | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0212395 A1 | 11/2003 | Woloszko et al. | 606/32 |
| 2003/0212396 A1 | 11/2003 | Eggers et al. | 606/41 |
| 2004/0024399 A1 | 2/2004 | Sharps et al. | 606/32 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/41 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Hovda et al. | 606/32 |
| 2006/0095031 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0001088 A1 | 1/2007 | Dahla | 606/41 |
| 2007/0010809 A1 | 1/2007 | Sanders et al. | 606/32 |

FOREIGN PATENT DOCUMENTS

| | | |
|---|---|---|
| DE | 3930451 A1 | 3/1991 |
| DE | 195 37 084 A1 | 10/1996 |
| DE | 29609350 | 10/1996 |
| DE | 296 19 029 U1 | 5/1997 |
| EP | 182689 | 5/1986 |
| EP | 292621 | 11/1988 |
| EP | 515 867 | 12/1992 |
| EP | 0703461 | 3/1996 |
| EP | 0 553 576 B1 | 4/1996 |
| EP | 0740926 | 11/1996 |

| | | |
|---|---|---|
| EP | 0754437 | 1/1997 |
| EP | 812575 | 12/1997 |
| EP | 0 694 290 | 11/2000 |
| EP | 1 179 320 | 2/2002 |
| FR | 1514319 | 8/1968 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| RU | 2026640 | 1/1995 |
| WO | 90/03152 | 4/1990 |
| WO | WO 90/07303 | 7/1990 |
| WO | WO 92/21278 | 12/1992 |
| WO | WO 93/13816 | 7/1993 |
| WO | 93/20747 | 10/1993 |
| WO | 94/03134 | 2/1994 |
| WO | 94/04220 | 3/1994 |
| WO | 94/08654 | 4/1994 |
| WO | WO 94/14383 | 7/1994 |
| WO | 94/26228 | 11/1994 |
| WO | 95/05780 | 3/1995 |
| WO | 95/34259 | 12/1995 |
| WO | 96/00042 | 1/1996 |
| WO | 96/35469 | 11/1996 |
| WO | 96/39962 | 12/1996 |
| WO | 96/39963 | 12/1996 |
| WO | 96/39964 | 12/1996 |
| WO | 96/39965 | 12/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/25101 | 7/1997 |
| WO | 97/29803 | 8/1997 |
| WO | 97/32551 | 9/1997 |
| WO | 97/34540 | 9/1997 |
| WO | 97/44071 | 11/1997 |
| WO | 97/48345 | 12/1997 |
| WO | 97/48346 | 12/1997 |
| WO | 98/07468 | 2/1998 |
| WO | 98/17185 | 4/1998 |
| WO | 98/17186 | 4/1998 |
| WO | 98/19614 | 5/1998 |
| WO | 98/23324 | 6/1998 |
| WO | 98/27877 | 7/1998 |
| WO | 98/27879 | 7/1998 |
| WO | 98/27880 | 7/1998 |
| WO | 98/30144 | 7/1998 |
| WO | 98/38925 | 9/1998 |
| WO | 98/39038 | 9/1998 |
| WO | 98/56324 | 12/1998 |
| WO | 99/09919 | 3/1999 |
| WO | 99/49799 | 10/1999 |
| WO | 99/51155 | 10/1999 |
| WO | 99/51158 | 10/1999 |
| WO | 01/87154 | 5/2001 |
| WO | 02/36028 | 5/2002 |
| WO | 93/13816 | 7/2003 |
| WO | 2005/125287 | 12/2005 |

OTHER PUBLICATIONS

Mirhoseini et al. (1993) *J. of Clinical Laser Medicine & Surgery* 11(1):15-19. Transmyocardial Laser Revascularization: A Review.
Mirhoseini et al. (1988) *Ann Thorac Surg* 45:415-420. New Concepts in Revascularization of the Myocardium.
Sen et al. (1965) *J. Thoracic and Cardiovascular Surgery* 50 (2) :181-189. Transmyocardial acupuncture.
Whittaker et al. (1996) *Circulation* 93 (1) :143-152. Transmural Channels Can Protect Ischemic Tissue.
Hardy et al. (1990) *Basic Research in Cardiology* 85:179-196. Regional myocardial blood flow and cardic mechanics in dog hearts with $CO_2$ laser-induced intramyocardial revascularization.
Walter et al. (1971) *Europ. Surg. Res.* 3:130-138. Tratment of Acute Mycardial Infarction by Transmural Blood Supply from the Ventricular Cavity.
Mirhoseini et al. (1981) *J. of Microsurgery* 2:253-260. Revascularization of the Heart by Laser.
Mirhoseini et al. (1982) *Lasers in Surgery and Medicine* 2:187-198. Transventricular Revascularization by Laser.
C. Slager et al. (1987) *Z. Kardiologie* 76 (6) :67-71.
C. Slager et al. (1985) *JACC* 5(6) :1382-6.
P. Nardella (1989) *SPIE* 1068:42-49.
Elsasser et al. (1976) *Medizinal-Markt/Acta Medicotechnica* 24 (4) :129-134.
E. Kramolowsky et al. (1991) *J. of Urology* 146:669-674.
R. Tucker et al. (1990) *Urol. Res.* 18:291-294.
R. Tucker et al. (1989) *J. of Urology* 141:662-665.
R. Tucker et al. (1989) Abstract P14-11, 7th World Congress on Endourology and ESWL, Nov. 27-30, 1989, Kyoto, Japan.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-II Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engieering* vol. 4, pp. 206-216, May 1969.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs, Jan. 24, 1991.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg, 1995.

Malis, L., "Instrumentation for Microvascular Neurosurgery" *Cerebrovascular Surgery*, vol. 1, pp. 245-260, 1985.

Malis, L., "New Trends in Microsurgery and Applied Technology," *Advanced Technology in Neurosurgery*, pp. 1-16, 1988.

Malis, L., "The Value of Irrigation During Bioploar Coagulation" See ARTC 21602, 1 pg, Apr. 9, 1993.

O'Malley, Schaum's Outline of Theory and Problems of Basic Circuit Analysis, McGraw-Hill, 2nd Ed., pp. 3-5, 1992.

Olsen MD, Bipolar Laparoscopic Cholecstectomy Lecture (marked confidential), 12 pgs, Oct. 7, 1991.

Pearce, John A. "Electrosurgery", pp. 17, 69-75, 87, John Wiley & Sons, New York, 1986.

Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" *Gastroenterology* vol. 74(3), pp. 527-534, 1978.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Ramsey et al., "A Comparison of Bipolar and Monopolar Diathermy Probes in Experimental Animals", *Urological Research* vol. 13, pp. 99-102, 1985.

Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.

Shuman, "Bipolar Versus Monopolar Electrosurgery: Clinical Applications," *Dentistry Today*, vol. 20, No. 12, 7 pgs, Dec. 2001.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engieering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. Mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al., "Demodulated Low Frequency Currents from Electrosurgical Procedures," *Surgery, Gynecology and Obstetrics*, 159:39-43, 1984.

Valley Forge Scientific Corp., "Summary of Safety and Effective Information from 510K", 2pgs, 1991.

Valley Forge's New Products, CLINICA, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Mirhoseini et al., "New Concepts in Revascularization of the Myocardium", Ann Thorac Surg 45:415-420, 1988.

Mirhoseini et al., "Revascularization of the heart by Laser", J. of Microsurgery 2:253-260, 1981.

Rand et al., "Effect of Elecctrocautery on Fresh Human Articular Cartilage", J. Arthro. Surg., vol. 1, pp. 242-246, 1985.

Salter, L.F., "Remedies for In-Stent Restenosis", Catheterization and Cardiovascular Diagnosis 37:320-321, 1996.

Sen, J. et al., "Transyocardial Acupuncture", Thoracic and Cardiovascular Surgery 50(2):181-189, 1965.

Topaz, O., "The Stenotic Stent: Mechanisms and Revascularization Options", Catheterization and Cardiovascular Diagnosis 37:293-299, 1996.

Whittaker et al., "Transmural Channels Can Protect Ischemic Tissue", Circulation 93(1):143-152, 1996.

European Search Report for EP 01127084 3pgs Mailed Oct. 7, 2003.

PCT International Search Report for PCT/US92/11265 1 page, Mailed Jun. 11, 1993.

PCT Written Opinion for PCT/US92/11265 4 pgs, Mailed Jul. 8, 1994.

PCT Notification of Transmittal of the International Search Report for PCT/US96/18651 4 pgs, Mailed Jan. 30, 1997.

PCT Notification of Transmittal of the International Preliminary Examination Report for PCT/US96/18651 4 pgs, Mailed Sep. 22, 1997.

PCT Notification of Transmittal of the International Search Report for PCT/US98/07976 4 pgs, Mailed Aug. 20, 1998.

PCT Notification of Transmittal of the International Preliminary Examination Report for PCT/US98/07976 4 pgs, Mailed Jun. 9, 1999.

PCT Notification of Transmittal of the International Search Report for PCT/US98/17703 4 pgs, Mailed Nov. 12, 1998.

PCT Written Opinion for PCT/US98/17703 5 pgs, Mailed Aug. 11, 1999.

PCT Notification of Transmittal of the International Search Report for PCT/US99/06808 4 pgs, Mailed May 27, 1999.

PCT Written Opinion for PCT/US99/06808 4 pgs, Mailed Jan. 18, 2000.

Cumberland, D.C. et al., "Percutaneous Laser Thermal Angioplasty: Initial Clinical Results with a Laser Probe in Total Peripheral Artery Occlusions," *Lancet*, pp. 1457-1459.

Dotter, C.T. et al., "Transluminal Treatment of Arteriosclerotic Obstruction: Description of a New Technic and Preliminary Report of its application," *Circulation*, vol. 30, pp. 654-670.

Faxon, D.P. et al., In Vivo Evaluation of Athrectomy, A New Technique to Enlarge Atherosclerotic Vessels, *Abstracts of the 58th Scientific Sessions Circulation*, 72 III-469.

Gruntzig, A.R. et al., "Nonoperative Dilatation of Coronary-Artery Stenosis: Percutaneous Translumical Coronary Angioplasty," *New England Journal of Med.*, vol. 301, pp. 61-68.

Kensey et al., "Recanalization of Obstructed Arteries Using a Flexible Rotating Tip Catheter," *Abstracts of the 59th Scientific Sessions, Circulation*, II-457.

Meier, B. et al., "Repeat Coronary Angioplasty," *Journal of American College of Cardiology*, vol. 4, pp.463-466.

Simpson, J.B. et al., "Transluminal Atherectomy: Initial Clinical Results in 27 Patients," *Abstracts of the 59th Scientific, Circulation*, 74 II-203.

Simpson, J.B. et al., "Transluminal Atherectomy: Results in 21 Human Cadaver Vascular Segments," *Abstracts of the 59th Scientific, Circulation*, 74 II-204.

* cited by examiner

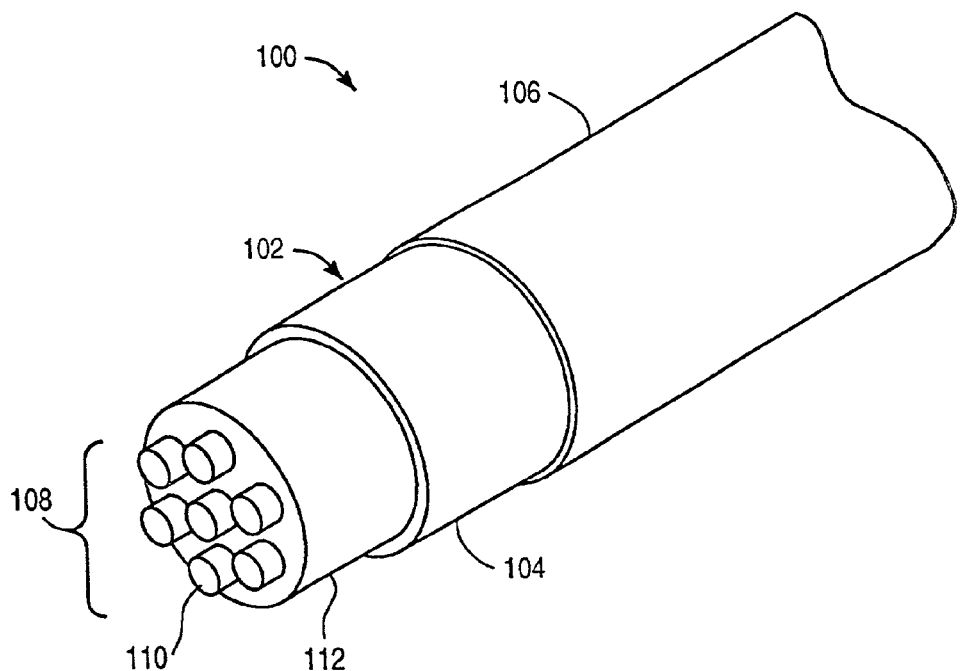
FIG. 3
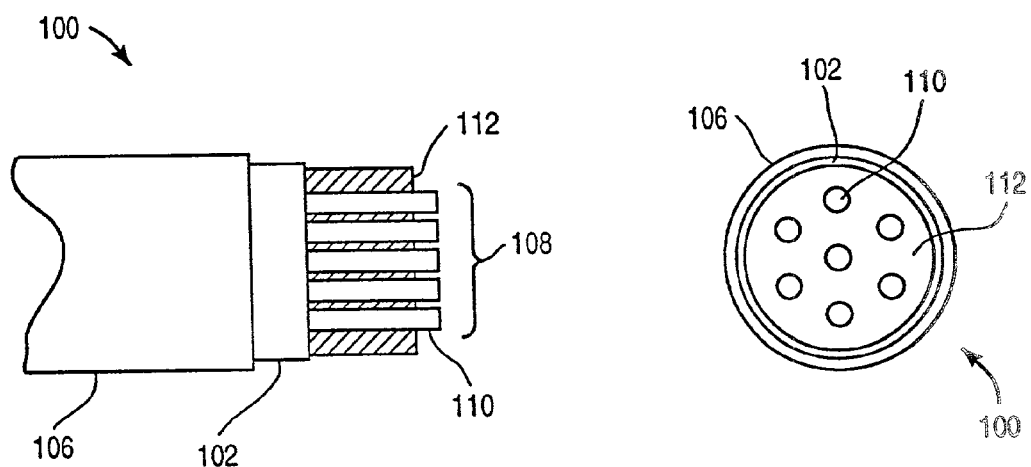
FIG. 4A
FIG. 4B

SYSTEM FOR ELECTROSURGICAL MYOCARDIAL REVASCULARIZATION

The present invention is a divisional of application Ser. No. 09/054,660 filed Apr. 3, 1998 now abandoned, which is a continuation of application Ser. No. 08/753,227 filed Nov. 22, 1996, now U.S. Pat. No. 5,873,855, which is a continuation-in-part of application Ser. No. 08/562,331 filed Nov. 22, 1995, now U.S. Pat. No. 5,683,366 which is a continuation-in-part of application Ser. No. 08/485,219 filed Jun. 7, 1995, now U.S. Pat. No. 5,697,281, which was a continuation-in-part of PCT International Application, US National Phase Serial No. PCT/US94/05168 filed May 10, 1994, which was a continuation-in-part of U.S. patent application Ser. No. 08/059,681, filed on May 10, 1993, now abandoned, which was a continuation-in-part of U.S. application Ser. No. 07/958,977, filed on Oct. 9, 1992, now U.S. Pat. No. 5,366,443 which is a continuation-in-part of U.S. application Ser. No. 07/817,575, filed on Jan. 7, 1992, now abandoned, the full disclosures of which are incorporated herein by reference for all purposes.

BACKGROUND OF THE INVENTION

Field of the Invention

The present invention relates generally to the field of electrosurgery and, more particularly, to surgical devices and methods that employ high frequency energy to cut and ablate heart tissue for increasing the flow of blood to a patient's heart.

Coronary artery disease, the build up of atherosclerotic plaque on the inner walls of the coronary arteries, causes the narrowing or complete closure of these arteries resulting in insufficient blood flow to the heart. A number of approaches have been developed for treating coronary artery disease. In less severe cases, it is often sufficient to treat the symptoms with pharmaceuticals and lifestyle modification to lessen the underlying causes of the disease. In more severe cases a coronary artery blockage can often be treated using endovascular techniques, such as balloon angioplasty, a laser recanalization, placement of stents, and the like.

In cases where pharmaceutical treatment and endovascular approaches have failed or are likely to fail, it is often necessary to perform a coronary artery bypass graft procedure using open or thoracoscopic surgical methods. For example, many patients still require bypass surgery due to such conditions as the presence of extremely diffuse stenotic lesions, the presence of total occlusions and the presence of stenotic lesions in extremely tortuous vessels. However, some patients are too sick to successfully undergo bypass surgery. For other patients, previous endovascular and/or bypass surgery attempts have failed to provide adequate revascularization of the heart muscle.

The present invention is particularly concerned with an alternative to the above procedures, which is known as laser myocardial revascularization (LMR). LMR is a recent procedure developed with the recognition that myocardial circulation occurs through arterioluminal channels and myocardial sinusoids in the heart wall, as well as through the coronary arteries. In LMR procedures, artificial channels are formed in the myocardium with laser energy to provide blood flow to ischemic heart muscles by utilizing the heart's ability to perfuse itself from these artificial channels through the arterioluminal channels and myocardial sinusoids. In one such procedure, a $CO_2$ laser is utilized to vaporize tissue and produce channels in the heart wall from the epicardium through the endocardium to promote direct communication between blood within the ventricular cavity and that of existing myocardial vasculature. The laser energy is typically transmitted from the laser to the epicardium by an articulated arm device. Recently, a percutaneous method of LMR has been developed in which an elongated flexible lasing apparatus is attached to a catheter and guided endoluminally into the patient's heart. The inner wall of the heart is irradiated with laser energy to form a channel from the endocardium into the myocardium for a desired distance.

While recent techniques in LMR have been promising, they also suffer from a number of drawbacks inherent with laser technology. One such drawback is that the laser energy must be sufficiently concentrated to form channels through the heart tissue, which reduces the diameter of the channels formed by LMR. In addition, free beam lasers generally must completely form each artificial lumen or revascularizing channel during the still or quiescent period of the heart beat. Otherwise, the laser beam will damage surrounding portions of the heart as the heart beats and thus moves relative to the laser beam. Consequently, the surgeon must typically form the channel in less than about 0.08 seconds, which requires a relatively large amount of energy. This further reduces the size of the channels that may be formed with a given amount of laser energy. Applicant has found that the diameter or minimum lateral dimension of these artificial channels may have an effect on their ability to remain open. Thus, the relatively small diameter channels formed by existing LMR procedures (typically on the order of about 1 mm or less) may begin to close after a brief period of time, which reduces the blood flow to the heart tissue.

Another drawback with current LMR techniques is that it is difficult to precisely control the location and depth of the channels formed by lasers. For example, the speed in which the revascularizing channels are formed often makes it difficult to determine when a given channel has pierced the opposite side of the heart wall. In addition, the distance in which the laser beam extends into the heart is difficult to control, which can lead to laser irradiation with heating or vaporization of blood or heart tissue within the ventricular cavity. For example, when using the LMR technique in a pericardial approach (i.e., from outside surface of the heart to inside surface), the laser beam may not only pierce through the entire wall of the heart but may also irradiate blood within the heart cavity. As a result, one or more blood thromboses or clots may be formed which can lead to vascular blockages elsewhere in the circulatory system. Alternatively, when using the LMR technique in an endocardial approach (i.e., from the inside surface of the heart toward the outside surface), the laser beam may not only pierce the entire wall of the heart but may also irradiate and damage tissue surrounding the outer boundary of the heart.

2. Description of the Background Art

Devices incorporating radio frequency electrodes for use in electrosurgical and electrocautery techniques are described in Rand et al. (1985) *J. Arthro. Surg.* 1:242-246 and U.S. Pat. Nos. 5,281,216; 4,943,290; 4,936,301; 4,593,691; 4,228,800; and 4,202,337. U.S. Pat. Nos. 4,943,290 and 4,036,301 describe methods for injecting non-conducting liquid over the tip of a monopolar electrosurgical electrode to electrically isolate the electrode, while energized, from a surrounding electrically conducting irrigant. U.S. Pat. Nos. 5,195,959 and 4,674,499 describe monopolar and bipolar electrosurgical devices, respectively, that include a conduit for irrigating the surgical site.

U.S. Pat. Nos. 5,380,316, 4,658,817, 5,389,096, PCT Application No. WO 94/14383, European Patent Application No. 0 515 867, and Articles "Transmyocardio Laser Revascularization", Mirhoseini et al., *Journal of Clinical Laser*

Medicine & Surgery Vol. 11, No. 1:15-19 (1993); "New Concepts in Revascularization of the Myocardium", Mirhoseini, et al., *The Annuals of Thoracic Surgery Society of Thoracic Surgeons*, Vol. 45, No. 4:415-420 (1988); "Transmyocardial Acupuncture", Sen, et al. *Journal of Thoracic and Cardiovascular Surgery*, Vol. 50, No. 2:181-189 (1965); "Transmural Channels Can Protect Ischemic Tissue", Whittaker, et al. *Circulation*, Vol. 93, No. 1:143-152 (1996); "Regional myocardial blood flow and cardiac mechanics in dog hearts with $CO_2$ laser-induced intramyocardial revascularization", Hardy, et al., *Basic Res. Cardiol*, 85:179-196 (1990); "Treatment of Acute Myocardial Infarction by Transmural Blood Supply From the Ventricular Cavity", Walter, et al., *Europ. Sure. Res.*, 130-138 (1971); "Revascularization of the Heart by Laser", Mirhoseini and Clayton, *Journal of Microsurgery*, 2:253-260 (1981); "Transventricular Revascularization by Laser", Mirhoseini, et al., *Lasers in Surgery and Medicine*, 2:187-198 (1982) describe methods and apparatus for percutaneous myocardial revascularization. These methods and apparatus involve directing laser energy against the heart tissue to form transverse channels through the myocardium to increase blood flow from the ventricular cavity to the myocardium.

SUMMARY OF THE INVENTION

The present invention provides systems, apparatus and methods for selectively applying electrical energy to structures within or on the surface of a patient's body. The present invention allows the surgical team to perform electrosurgical interventions, such as ablation and cutting of body structures, while limiting the depth of necrosis and limiting damage to tissue adjacent the treatment site. The systems, apparatus and methods of the present invention are particularly useful for canalizing or boring channels or holes through tissue, such as the ventricular wall of the heart during transmyocardial revascularization procedures.

In a method according to the present invention, an active electrode surface is positioned in close proximity to a target site on the wall of a patient's heart, and high frequency voltage is applied between the active voltage surface and a return electrode to ablate tissue at the heart wall. The high frequency voltage ablates, i.e. volumetrically removes the heart tissue, and the electrode surface is axially translated into the space vacated by the removed tissue to bore a channel through the heart tissue. The active electrode surface may be introduced into the thoracic cavity and placed adjacent the outer heart wall or epicardium to form an inward channel toward the ventricular cavity, or it may be delivered into the ventricular cavity of the heart and positioned adjacent the inner heart wall or endocardium to form a channel extending outward towards the epicardium. In either case, the channels formed through the heart wall promote direct communication between blood within the ventricular cavity and that of existing myocardial vasculature to increase blood flow to the heart tissue.

One of the advantages of the present invention, particularly over previous methods involving lasers, is that the surgeon can more precisely control the location, depth and diameter of the revascularizing channels formed in the heart tissue. For example, the active electrode surface remains in contact with the heart wall as the high frequency voltage ablates the heart tissue (or at least substantially close to the heart wall, e.g., usually on the order of about 0.1 to 2.0 mm and preferably about 0.1 to 1.0 mm). This preserves tactile sense and allows the surgeon to more accurately determine when to terminate cutting of a given channel so as to minimize damage to surrounding tissues and/or minimize bleeding into the thoracic cavity. In addition, axially translating the active electrode through the heart wall allows the surgeon to form the channel at a slower pace than conventional LMR because the channel does not have to be completely formed during the quiescent or diastolic period of the heart. Since the active electrode array generally directs tissue ablating energy only about 0.1 to 3.0 mm in front of the electrode array (and preferably only about 0.1 to 2.0 mm in front of the electrode array), this relatively slow ablation pace allows the surgeon to more accurately control the channel depth.

In one embodiment, an electrosurgical probe having one or more electrodes on its distal end is delivered into the thoracic cavity exterior to the heart wall. The probe may be delivered directly through a median thoracotomy or through an intercostal percutaneous penetration, such as a cannula or trocar sleeve in the chest wall between two adjacent ribs. The electrode or electrode array is then positioned in close proximity to the epicardium in the region of the heart to be canalized, and a high frequency voltage is applied between the electrode or electrode array and a return electrode to form artificial channels through the heart tissue. The return electrode may be integral with the probe. By way of example, the return electrode may be located on the perimeter of the probe shaft proximal to the ablating (active) electrode or electrode array. In another embodiment, two or more electrodes of opposite polarity may be positioned at the distal end of the electrosurgical probe to effect ablation of the wall of the heart. Alternatively, the return electrode may be positioned on another instrument that is, for example, delivered through the same or another intercostal trocar sleeve. The probe is axially translated through the artificial channel provided by the trocar sleeve as the active electrode ablates tissue to maintain contact with the heart wall and to facilitate precise control of the procedure by the surgeon.

In another embodiment, the electrode array is introduced through a percutaneous penetration in the patient and axially translated through one of the major arterial vessels to the left ventricular cavity. In this embodiment, the electrode or electrode array may form a distal portion of an electrosurgical catheter and may be guided through a conventional or specialized guide catheter. The electrode array is then positioned adjacent the endocardium and axially translated outward to form one or more channels through the myocardium. The surgeon may control the depth of the channels by axially translating the catheter through the heart wall, and terminating the electrical energy to the active array when the channel has reached the desired depth. The channels may be formed completely through the myocardium to the outer surface of the epicardium, or the surgeon may terminate the electrical energy prior to penetrating the outer surface of the epicardium to prevent blood from flowing into the thoracic cavity.

The control of the depth of channel formed in the wall of the heart may be accomplished using one or a combination of several methods and apparatus. By way of example, real-time fluoroscopic visualization of the heart in combination with radiopaque markers on the electrosurgical catheter may be used by the surgeon to control the depth of the channel and terminate ablation before penetrating through the outer surface of the heart wall. Alternatively, ultrasound methods may be incorporated within the electrosurgical catheter or guide tube to determine the thickness of the heart wall adjacent to the distal probe tip and allow the surgeon to pre-set the depth of each channel before energizing the probe and ablating the heart tissue. Also, ultrasound methods may be incorporated within the electrosurgical catheter to continuously detect the distance of the electrode or electrode array from the outer surface of the heart and to interrupt the voltage applied to the ablating electrode(s) in order to stop the forward advance of the catheter at a predetermined distance from the outer surface of the heart. In yet another embodiment, the electrosurgical catheter includes a small diameter tissue electrical impedance measurement sensor (e.g., 0.1 to 0.5 mm diameter) which extends distal to the tissue ablating electrode or electrode array (e.g., 1 to 10 mm). This impedance measurement sensor detects the outer surface of the heart as it penetrates through the tissue and enters a region of different electrical impedance (i.e., the fluid-filled cavity surrounding the heart).

In another aspect of the present invention, radially expandable luminal protheses, such as stents and stent-grafts, are implanted in one or more of the revascularizing channels after the channels have been formed by the electrosurgical instrument. The stents may be implanted immediately after the channels have been formed (i.e., with the electrosurgical probe or catheter), or they may be implanted after the channels have been formed with a separate delivery catheter. The stents are compressed into a narrow-diameter configuration, and advanced endoluminally to the target site in the heart tissue with a delivery catheter. The intraluminal prostheses will typically comprise a resilient, radially compressible, tubular frame having a proximal end, a distal end, and an axial lumen therebetween. The tubular frame includes a plurality of openings or slots that allow it to be expanded radially outward within the channel by conventional methods, such as shape memory alloys, expandable balloons, and the like. The stent exerts a radial force against the inner channel walls to maintain patency of the channels, thereby increasing the blood flow from the ventricular cavity to the myocardium. In the case of stent-grafts, a porous liner, typically a fabric, polymeric sheet, membrane, or the like, will line all or most of the luminal surface of the tubular frame to inhibit occlusion of the channel through the openings in the tubular frame while allowing oxygenated blood to pass through the porous liner and into the heart tissues surrounding the channel.

The apparatus according to the present invention comprises an electrosurgical instrument having a shaft with a proximal end, a distal end and one or more active electrodes at or near the distal end. A return electrode is disposed on the shaft close to the distal end and a connector extends through the shaft for electrically coupling the active return electrodes to a high frequency voltage source. The distal portion of the shaft and the active electrodes are sized for delivery through a trocar canalization (e.g., pericardial approach) or guiding catheter (e.g., endocardial approach) to ablate tissue in the heart wall to form a revascularizing channel through at least a portion of the heart wall. The return electrode may be provided integral with the shaft, or it may be separate from the shaft.

The shaft may also incorporate means for delivery of electrically conductive liquid (e.g., isotonic saline) to the distal end of the electrosurgical instrument to provide an electrically conductive pathway between the one or more active electrodes and the return electrode. The electrosurgical instrument may also include an ultrasonic transducer for either measuring the thickness of the heart wall (for presetting the depth of canalization) or detecting the distance from the distal end of the electrosurgical instrument to the outer surface of the heart to interrupt the ablation of the heart wall (and depth of canalization) at a preselected distance from the outer surface of the heart wall using active feedback control within the power source. Alternatively, the electrosurgical instrument may include an electrical impedance measuring sensor for detecting the distance form the distal end of the electrosurgical instrument to the outer surface of the heart to interrupt the ablation of the heart wall (and depth of canalization) at a preselected distance from the outer surface of the heart wall using active feedback control with the power source (e.g., when the measured electrical impedance at the tip of the sensor increases above a preselected level, the applied voltage is interrupted).

In an exemplary embodiment, the instrument comprises an electrosurgical probe having at least a distal end configured for delivery through an intercostal penetration in the patient, such as a trocar sleeve positioned between two ribs. The probe preferably includes an electrode array with a plurality of isolated electrode terminals at its distal end. A return electrode is proximally recessed from the electrode array for applying high frequency voltage therebetween to ablate or bore a hole through the heart tissue. The probe may include a fluid channel for directing electrically conducting fluid to the target site to complete the current return path from the heart tissue to the return electrode. Alternatively, this path may be completed by the heart tissue on the side of the probe, or the blood and other fluids existing within the heart wall.

In another embodiment, the electrosurgical instrument comprises a guide catheter having a flexible, steerable shaft configured for endoluminal delivery into the ventricular cavity. The guide catheter provides an interior lumen through which an electrosurgical catheter can be deployed percutaneously to form a channel in the wall of the heart. The guide catheter is first positioned on the endocardial surface of the heart at the site of a required channel. Next, the electrosurgical catheter located within the lumen of the guide catheter is positioned against the surface of the endocardium and energized while advancing to a preselected channel depth based on one or a combination of the channel depth controlling methods described above. Similar to the probe embodiment, the electrosurgical catheter will preferably include an electrode array of isolated electrode terminals at it distal end, and a return electrode proximally recessed from the electrode array. Alternatively, the electrosurgical catheter described above may be guided into the heart and into the desired position using a steerable catheter body which eliminates the need for a separate steerable guiding catheter.

In an exemplary embodiment, the electrode array at the distal end of the probe or catheter is configured such that current flow from at least two of the electrode terminals is independently controlled based on the electrical impedance between the electrode terminal and the return electrode. Each individual electrode terminal in the electrode array is electrically connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current limiting elements, such as inductors, capacitors, resistors and/or combinations thereof, such as resonant circuits. The current limiting elements may be provided in the probe, connectors, cable, controller or along the conductive path from the controller to the distal tip. In addition to the control of power delivery to the electrodes to effect ablation of the target tissue (e.g., heart wall) while limiting power delivery when low electrical resistivity material is encountered (e.g., blood), electrosurgical catheter (when employed percutaneously) may incorporate ultrasonic and/or tissue impedance measuring sensor which serve to interrupt power delivery when a preselected channel depth or remaining (uncanalized) wall thickness is reached.

In another aspect of the invention, an electrosurgical system includes the electrosurgical probe or catheter as described above together with an electrosurgical generator and a delivery mechanism for positioning a radially expandable luminal prothesis into the revascularizing channels formed by the electrosurgical probe or catheter. The delivery mechanism may be integral with the electrosurgical instrument, or part of a separate delivery catheter. The separate delivery catheter usually includes an elongate flexible shaft structure having a proximal end and a distal end. The shaft structure includes a prosthesis receptacle near the distal end in or over which a radially compressible tubular prosthesis is carried during maneuvering of the shaft and prosthesis within an anatomical lumen. The luminal prostheses will typically comprise a resilient, radially compressible, tubular frame having a plurality of openings or slots that allow it to be expanded radially outward into an enlarged configuration. The stent exerts a radial force against the inner channel walls to maintain lumen patency and/or mechanically augment luminal wall strength, thereby maintaining the blood flow from the ventricular cavity to the myocardial tissue.

In yet another aspect of the invention, an instrument guidance system is provided for detecting an "end point" for each artificial channel and/or for determining appropriate target sites on the heart wall for forming the artificial channels. The instrument guidance system will preferably allow a surgeon to determine when the electrosurgical instrument is near the other end of the heart wall (i.e., the outer surface of the epicardium or the inner surface of the endocardium). In the case of the percutaneous approach in which ablation begins at the endocardium, the detection system indicates to the surgeon to stop axially translating the probe so that the probe does not form a channel completely through a heart wall, which limits bleeding and reduces damage to surrounding tissue structures located at or near the outer surface of the heart. In addition, the guidance system will preferably allow the surgeon to determine an appropriate target site on the heart wall to form the channel to avoid accidental puncturing of relatively large vessels in the heart wall. The guidance system may include a fiberoptic viewing system or an ultrasound guidance system for determining the target sites, and/or current limiting circuitry that detects when the probe is adjacent blood vessels and/or the outer or inner edges of the heart wall.

A further understanding of the nature and advantages of the invention will become apparent by reference to the remaining portions of the specification and drawings.

BRIEF DESCRIPTION OF THE DRAWINGS

FIG. 3 is a perspective view of the distal tip of another electrosurgical probe that does not incorporate a fluid lumen for delivering electrically conducting liquid to the target site;

FIG. 4A is an enlarged, cross-sectional view of the distal tip of the electrosurgical probe of FIG. 3 illustrating an electrode array;

FIG. 4B is an end view of the distal tip of the electrosurgical probe of FIG. 3;

DESCRIPTION OF THE PREFERRED EMBODIMENT

Figure 1:
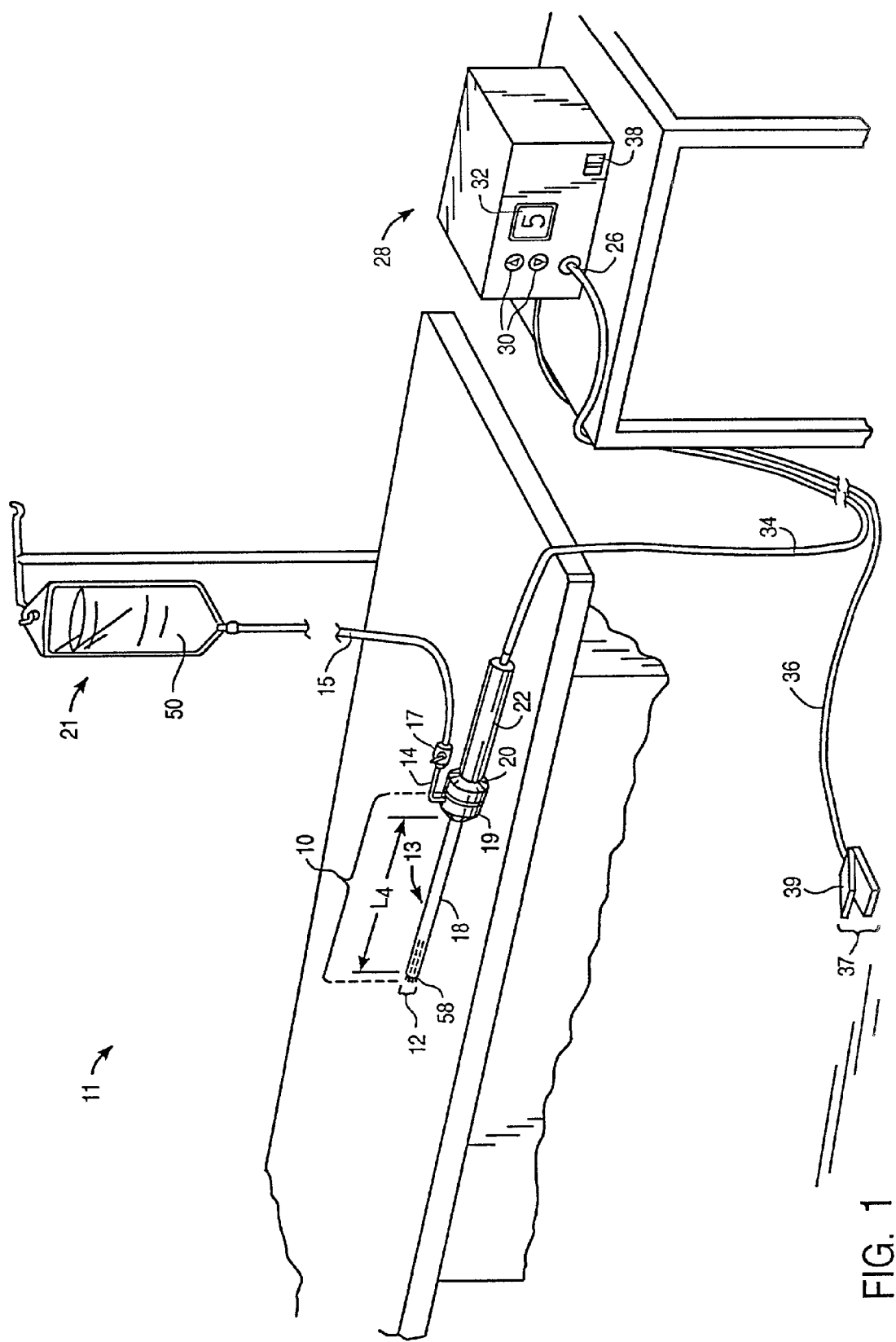
FIG. 1 is a perspective view of the electrosurgical system including an electrosurgical probe, an electrically conducting liquid supply and an electrosurgical power supply constructed in accordance with the principles of the present invention.

The present invention provides a system and method for selectively applying electrical energy to a target location within or on a patient's body. In particular, the present invention provides systems, devices and methods for increasing the blood flow to the heart by creating artificial channels or lumens through the myocardium of the heart. It will, however, be appreciated that the systems, devices and methods can be applied equally well to procedures involving other tissues of the body, as well as to other procedures including open surgery, laparoscopic surgery, thoracoscopic surgery, and other endoscopic surgical procedures.

The electrosurgical instrument will comprise a shaft having a proximal end and a distal end which supports an active electrode. The shaft may assume a wide variety of configurations, with the primary purpose being to mechanically support one or more active electrode and permit the treating physician to manipulate the electrode(s) from a proximal end of the shaft. Usually, an electrosurgical probe shaft will be a narrow-diameter rod or tube, more usually having dimensions which permit it to be introduced into a body cavity, such as the thoracic cavity, through an associated trocar or cannula in a minimally invasive procedure, such as arthroscopic, laparoscopic, thoracoscopic, and other endoscopic procedures. Thus, the probe shaft will typically have a length of at least 5 cm for open procedures and at least 10 cm, more typically being 20 cm, or longer for endoscopic procedures. The probe shaft will typically have a diameter of at least 1 mm and frequently in the range from 1 to 10 mm.

The electrosurgical probe may be delivered percutaneously (endoluminally) to the ventricular cavity of the heart by insertion through a conventional or specialized guide catheter, or the invention may include a catheter having an active electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The shaft will usually include a plurality of wires or other conductive elements running axially therethrough to permit connection of the electrode or electrode array and the return electrode to a connector at the proximal end of the shaft. Specific shaft designs will be described in detail in connection with the figures hereinafter.

The present invention may use a single electrode or an electrode array distributed over a distal contact surface of the electrosurgical instrument. In both configurations, the circumscribed area of the electrode or electrodes array will generally depend on the desired diameter of the revascularizing channel in the heart. For example, applicant has found that smaller diameter channels tend to remain patent for a shorter period of time than larger diameter channels. Thus, a relatively large diameter channel (on the order of about 1.5 to 3.0 mm) may be desired to improve lumen patency. The ability to select the diameter of the artificial channels is one of the advantages of the present invention over existing LMR procedures, which are typically limited by the concentration of light that is required to generate sufficient energy to ablate the tissue during the still or quiescent period of the heart (i.e., about 0.08 seconds). Usually, the area of the electrode array is in the range from 0.25 $mm^2$ to 20 $mm^2$, preferably from 0.5 $mm^2$ to 10 $mm^2$, and more preferably from about 0.5 $mm^2$ to 5.0 $mm^2$. In addition, the shape of the array and the distal end of the instrument shaft will also depend on the desired surface area of the channel. For example, the ratio of the perimeter of the electrode array to the surface area may be maximized to increase blood flow from the channel to the surrounding myocardial tissue. The electrode or electrodes may take the form of a solid round wire or other solid cross-sectional shapes such as squares, rectangles, hexagons, triangles, star-shaped or the like to provide additional edges around the distal perimeter of the electrodes. Alternatively, the electrode or electrodes may be in the form of hollow metal tubes having a cross-sectional shape which is round, square, hexagonal, rectangular or the like. The envelop or effective diameter of the individual electrode or electrodes ranges from about 0.05 to 3 mm, preferably from about 0.1 to 2 mm.

The electrode array will usually include at least two isolated electrode terminals, more usually at least four electrode terminals, preferably at least six electrode terminals, and often 50 or more electrode terminals, disposed over the distal contact surfaces on the shaft. By bringing the electrode array(s) on the contact surface(s) in close proximity with the target tissue and applying high frequency voltage between the array(s) and an additional common or return electrode in direct or indirect contact with the patient's body, the target tissue is selectively ablated or cut, permitting selective removal of portions of the target tissue while desirably minimizing the depth of necrosis to surrounding tissue.

As described above, the present invention may use a single active electrode or an electrode array distributed over a distal contact surface of an electrosurgical instrument, such as a probe, a catheter or the like. The electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In an exemplary embodiment, each individual electrode terminal in the electrode array is electrically insulated from all other electrode terminals in the array within said instrument and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current limiting elements, such as inductors, capacitors, resistors and/or combinations thereof. The current limiting elements may be provided in the probe, connectors, cable, controller or along the conductive path from the controller to the distal tip. A more complete description of a system and method for selectively limiting current to an array of isolated electrode terminals can be found in commonly assigned, co-pending application Ser. No. 08/561,958, filed Nov. 22, 1995, the complete disclosure of which has previously been incorporated herein by reference.

In a preferred aspect, this invention takes advantage of the differences in electrical resistivity between the target heart tissue and the surrounding conductive liquid (e.g., isotonic saline irrigant, blood or the like). By way of example, for any selected level of applied voltage, if the electrical conduction path between the common electrode and one of the individual electrode terminals within the electrode array is blood (having a relatively low electrical impedance), the current control means connected to the individual electrode will limit current flow so that the heating of intervening conductive liquid is minimized. On the other hand, if a portion of or all of the electrical conduction path between the common or return electrode and one of the individual electrode terminals within the electrode array is myocardial tissue (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

In the case of a single electrode, the invention may also use current limiting means to apply electrical energy selectively to the target tissue while limiting the unwanted application of electrical energy to the surrounding tissue. In this embodiment, the electrode may be connected to current limiting elements or to circuitry which limits or interrupts current flow to the electrode when low resistivity material (e.g., blood or electrically conductive saline irrigant) causes a lower impedance path between the common electrode and the electrode. The current limiting elements or circuitry may be configured to completely interrupt or modulate current flow to the electrode, for example, when a certain percentage of the electrode surface is in contact with low resistivity material. In one embodiment, the current flow will be modulated or completely interrupted when, for example, a large portion of the electrode surface is exposed to fluids and, therefore, not in contact with the target tissue. In this manner, current can be selectively applied to the target tissue, while minimizing current flow to surrounding fluids and adjacent non-target tissue structures.

In addition to the above described methods, the applicant has discovered another mechanism for ablating tissue while minimizing the depth of necrosis. This mechanism involves applying a high frequency voltage between the active electrode surface and the return electrode to develop high electric field intensities in the vicinity of the target tissue site. In this embodiment, the active electrode(s) include at least one active portion having a surface geometry configured to promote substantially high electric field intensities and associated current densities between the active portion and the target site when a high frequency voltage is applied to the electrodes. These high electric field intensities and current densities are sufficient to break down the tissue by processes including molecular dissociation or disintegration. The high frequency voltage imparts energy to the target site to ablate a thin layer of tissue without causing substantial tissue necrosis beyond the boundary of the thin layer of tissue ablated. This ablative process can be precisely controlled to effect the volumetric removal of tissue with minimal heating of or damage to surrounding or underlying tissue structures.

In an exemplary embodiment, the high electric field intensities at the active portion of the active electrode(s) may be generated by positioning the active electrode and target site within an electrically conducting liquid, such as isotonic saline or other body fluids, such as blood, and applying a high frequency voltage that is sufficient to vaporize the electrically conducting liquid over at least a portion of the active electrode in the region between the active portion of the active electrode and the target tissue. Since the vapor layer or vaporized region has a relatively high electrical impedance, it increases the voltage differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. A more detailed description of this phenomena can be found in application Ser. No. 08/561,958, filed on Nov. 22, 1995, the complete disclosure of which has already been incorporated herein by reference.

Suitable electrode surface geometries for producing sufficiently high electric field intensities to reach the threshold conditions for vapor layer formation may be obtained by producing sharp edges and/or corners at the active portion of the active electrode(s). Alternatively, the electrode(s) may be specifically designed to increase the edge/surface area ratio of the active portion through the use of shaped wires (e.g., square or hexagonal wires) or tubular electrodes offering high electric field intensities along the inside and outside perimeters of the tubular electrode. Additionally or alternatively, the active electrode surface(s) may be modified through chemical, electrochemical or abrasive methods to create a multiplicity of surface aspirates on the electrode surface. Suitable electrode designs for use with the present invention may be found in co-pending, commonly assigned application Ser. No. 08/687,792, filed Jul. 19, 1996, the complete disclosure of which is incorporated herein by reference.

The voltage applied between the common electrode and the electrode array will be at high or radio frequency, typically between about 5 kHz and 20 MHz, usually being between about 30 kHz and 2.5 MHz, and preferably being between about 50 kHz and 1 MHz. The RMS (root mean square) voltage applied will usually be in the range from about 5 volts to 1000 volts, preferably being in the range from about 50 volts to 800 volts, and more preferably being in the range from about 60 volts to 500 volts. These frequencies and voltages will result in peak-to-peak voltages and current that are sufficient to vaporize the electrically conductive liquid and, in turn, create the conditions within the vaporized region which result in high electric fields and emission of energetic photons and/or electrons to ablate tissue. Typically, the peak-to-peak voltage will be in the range of 40 to 4000 volts and preferably in the range of 100 to 3200 volts and more preferably in the range of 300 to 2400 volts.

As discussed above, the voltage is usually delivered in a waveform having a sufficiently high frequency (e.g., on the order of 5 kHz to 20 MHz) such that the voltage is effectively applied continuously (as compared with e.g., lasers claiming small depths of necrosis, which are generally delivered in brief pulses at a repetition rate of about 10 to 20 Hz). Hence, the duty cycle (i.e., cumulative time in any one-second interval that energy is applied) is on the order of about 50% for the present invention, as compared with lasers which typically have a duty cycle of about 0.001% to 0.0001%.

With the above voltage and current ranges, applicant has found that the electrosurgical instrument will usually bore a channel completely through the heart wall in about 0.5 to 20.0 seconds, preferably about 1.0 to 3.0 seconds, in the continuous mode and preferably about 10 to 15 seconds in the pulsed mode. It has been found that channels that are approximately 0.5 to 3.0 mm in diameter and approximately 1 to 4 cm deep may be easily and efficiently formed by this method, and that the revascularization procedure dramatically improves the flow of blood to the heart muscle.

The capability to form the desired channel over a longer period of time significantly reduces the amount of instantaneous power required to complete the channel. By way of example, $CO_2$ lasers used for LMR typically deliver the power for each channel within an elapsed time of 0.08 seconds. By contrast, the present invention can be used to complete the canalization of the same sized channel within about 1.0 second. As a result, the laser requires about 500 to 700 watts to form a 1 mm diameter channel while the present invention requires $\frac{1}{12}$ or about 42 to 58 watts to form the same channel. If larger channels are required, the power requirements increase by the square of the ratio of diameters. Hence, to produce a 2 mm channel in 0.08 seconds using a $CO_2$ laser, the required power will be four-fold higher or 2000 to 2800 watts which requires a very large and very expensive laser. In contrast, the present invention can form a 2 mm diameter channel (of the same length as above) in 1 second with an applied power of about 168 to 232 watts.

Usually, the current level will be selectively limited or controlled and the voltage applied will be independently adjustable, frequently in response to the resistance of tissues and/or fluids in the pathway between an individual electrode and the common electrode. Also, the applied voltage level may be in response to a temperature control means which maintains the target tissue temperature with desired limits at the interface between the electrode arrays and the target tissue. The desired tissue temperature along a propagating surface just beyond the region of ablation will usually be in the range from about 40° C. to 100° C., and more usually from about 50° C. to 60° C. The tissue being ablated (and hence removed from the operation site) immediately adjacent the electrode array may reach even higher temperatures. A temperature sensor may be incorporated within the distal end of the electrosurgical device to measure a temperature indicative of the nearby tissue beyond the ablation boundary.

The preferred power source of the present invention delivers a high frequency voltage selectable to generate average power levels ranging from tens of milliwatts to tens of watts per electrode, depending on the target tissue being ablated, the rate of ablation desired or the maximum allowed temperature selected for the probe tip. The power source allows the user to select the voltage level according to the specific requirements of a particular procedure.

The power source may be current limited or otherwise controlled so that undesired heating of electrically conductive fluids or other low electrical resistance media does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired ablation rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant).

As an alternative to such passive circuit structures, regulated current flow to each electrode terminal may be provided by a multi-channel power supply. An applied voltage with active current sensing circuitry is provided for each individual electrode terminal to control current within a range which will limit power delivery through a low resistance path, e.g., isotonic saline irrigant, and would be selected by the user to achieve the desired rate of cutting or ablation. Such a multi-channel power supply thus provides a voltage source with controlled current limits with selectable voltage level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during a given cycle.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

In yet another aspect of the invention, the control system is "tuned" so that it will not apply excessive power to the blood (e.g., in the left ventricle), once it crosses the wall of the heart and enters the chamber of the left ventricle. This minimizes the formation of a thrombus in the heart (i.e., will not induce thermal coagulation of the blood). The control system may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the probe can be used to detect the boundary between the wall of the heart and the blood filled left ventricle chamber, turning off the electrode array just as the probe crosses the boundary.

Referring to the drawings in detail, wherein like numerals indicate like elements, an electrosurgical system 11 is shown in FIG. 1 constructed according to the principles of the present invention. Electrosurgical system 11 generally comprises an electrosurgical instrument or probe or catheter 10 connected to a power supply 28 for providing high frequency voltage to electrosurgical instrument 10 and a liquid source 21 provided for supplying electrically conducting fluid 50 to probe 10.

In an exemplary embodiment as shown in FIG. 1, electrosurgical probe 10 includes an elongated shaft 13 which may be flexible or rigid, with flexible shafts optionally including support cannulas or other structures (not shown). It will be recognized that the probe shown in FIG. 1 will generally be employed in open or thoracoscopic procedures through intercostal penetrations in the patient. For endoluminal procedures into the ventricle, a delivery catheter 200 (FIGS. 6 and 11) will typically be employed, as discussed below. Probe 10 includes a connector 19 at its proximal end and an array 12 of electrode terminals 58 disposed on the distal tip of shaft 13. A connecting cable 34 has a handle 22 with a connector 20 which can be removably connected to connector 19 of probe 10. The proximal portion of cable 34 has a connector 26 to removably couple probe 10 to power supply 28. The electrode terminals 58 are electrically isolated from each other and each of the terminals 58 is connected to an active or passive control network within power supply 28 by means of a plurality of individually insulated conductors 42 (see FIG. 2A). Power supply 28 has a selection means 30 to change the applied voltage level. Power supply 28 also includes means for energizing the electrodes 58 of probe 10 through the depression of a pedal 39 in a foot pedal 37 positioned close to the user. The foot pedal 37 may also include a second pedal (not shown) for remotely adjusting the voltage level applied to electrodes 58. The specific design of a power supply which may be used with the electrosurgical probe of the present invention is described in parent application PCT US 94/051168, the full disclosure of which has previously been incorporated herein by reference.

Figure 2A:
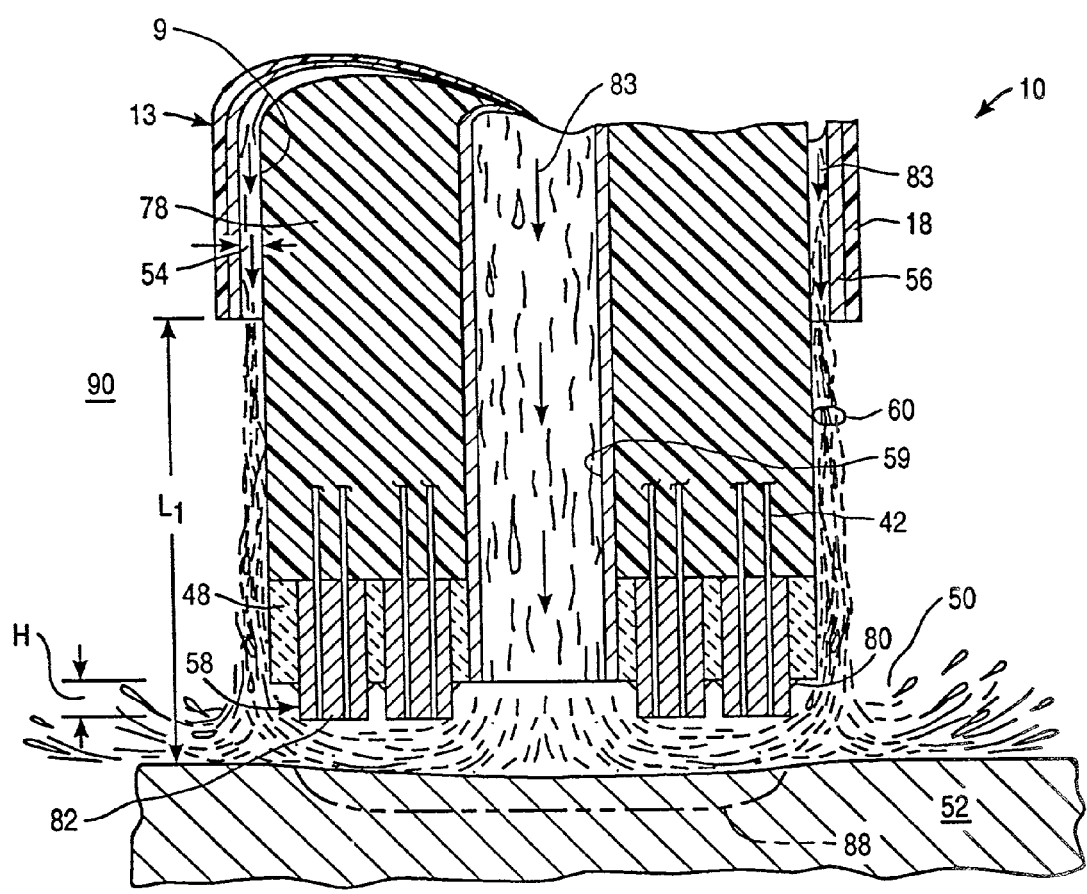
FIG. 2A is an enlarged, cross-sectional view of the distal tip of the electrosurgical probe of FIG. 1.
Figure 2B:
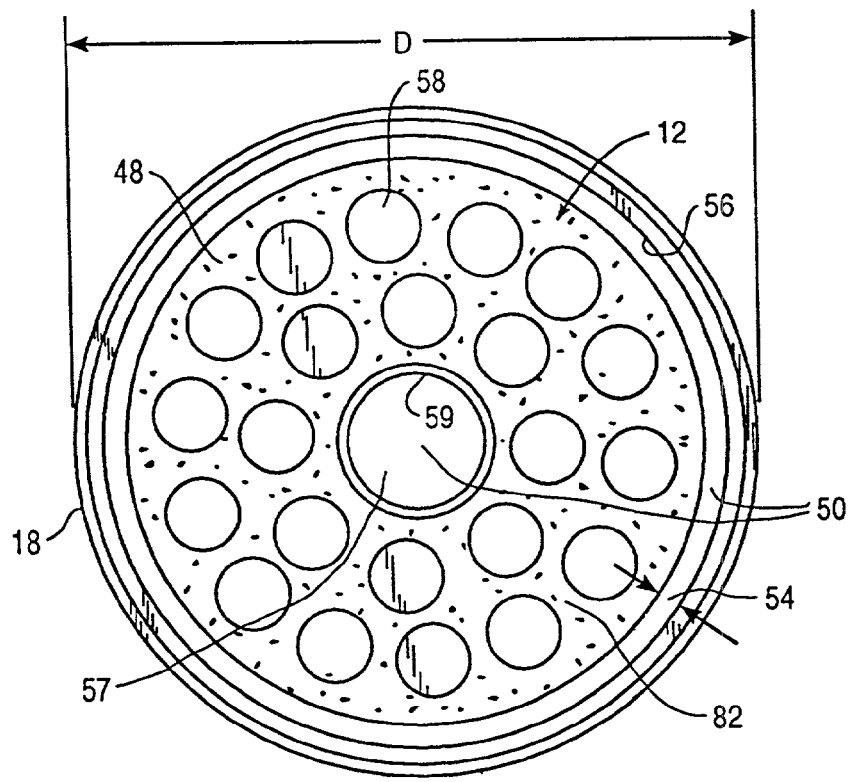
FIG. 2B is an end view of the electrosurgical probe of FIG. 1.
Figure 8:
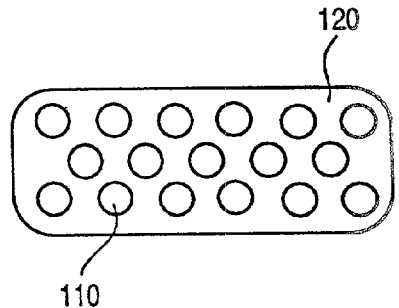

Referring to FIGS. 2A and 2B, the electrically isolated electrode terminals 58 are spaced-apart over an electrode array surface 82. The electrode array surface 82 and individual electrode terminals 58 will usually have dimensions within the ranges set forth above. In the preferred embodiment, the electrode array surface 82 has a circular cross-sectional shape with a diameter D (FIG. 2B) in the range from 0.3 mm to 4 mm. Electrode array surface 82 may also have an oval or rectangular shape, having a length L in the range of 1 mm to 20 mm and a width W in the range from 0.3 mm to 7 mm, as shown in FIG. 8 (discussed below). The individual electrode terminals 58 will protrude over the electrode array surface 82 by a distance (H) from 0 mm to 2 mm, preferably from 0 mm to 1 mm (see FIG. 2A).

The electrode terminals 58 are preferably composed of a electrically conductive metal or alloy, such as platinum, titanium, tantalum, tungsten, niobium, stainless steel, and the like. A preferred material for terminals 58 is tungsten because of its known biocompatibility and resistance to erosion under the application of high voltages. As shown in FIG. 2B, the electrode terminals 58 are anchored in a support matrix 48 of suitable insulating material (e.g., ceramic, glass/ceramic, or glass material, such as alumina, silica glass and the like) which could be formed at the time of manufacture in a flat, hemispherical or other shape according to the requirements of a particular procedure. In an exemplary embodiment, the support matrix 48 will comprise an inorganic insulator, such as ceramic, glass, glass/ceramic or a high resistivity material, such as silicon or the like. An inorganic material is generally preferred for the construction of the support matrix 48 since organic or silicone based polymers are known to rapidly erode during sustained periods of the application of high voltages between electrode terminals 58 and the return electrode 56 during tissue ablation. However, for situations in which the total cumulative time of applied power is less than about one minute, organic or silicone based polymers may be used without significant erosion and loss of material of the support matrix 48 and, therefore, without significant reduction in ablation performance.

As shown in FIG. 2A, the support matrix 48 is adhesively joined to support member 9, which extends most or all of the distance between matrix 48 and the proximal end of probe 10. In a particularly preferred construction technique, support matrix 48 comprises a plurality of glass or ceramic hollow tubes 400 (FIG. 2D) extending from the distal end of shaft 13. In this embodiment, electrode terminals 58 are each inserted into the front end of one of the hollow tubes 400 and adhered to the hollow tubes 400 so that the terminals 58 extend distally from each hollow tube 400 by the desired distance, H. The terminals 58 are preferably bonded to the hollow tubes 400 by a sealing material 402 (e.g., epoxy) selected to provide effective electrical insulation, and good adhesion to both the hollow tubes 400 and the electrode terminals 58. Alternatively, hollow tubes 400 may be comprised of a glass having a coefficient of thermal expansion similar to that of electrode terminal 58 and may be sealed around the electrode terminal 58 by raising the temperature of the glass tube to its softening point according to the procedures commonly used to manufacture glass-to-metal seals. Referring to FIG. 2D, lead wires 406, such as insulation 408 covered copper wires, are inserted through the back end of the hollow tubes 400 and coupled to the terminals 58 with a suitable conductive adhesive 404. The glass tube/electrode terminal assembly is then placed into the distal end of support member 9 to form the electrode array as shown in FIG. 2E. Alternatively, the lead wire 406 and electrode terminal 58 may be constructed of a single wire (e.g., stainless steel or nickel alloy) with insulation 408 removed over the length of the wire inserted into the hollow tube 400. As before, sealing material 402 is used to seal annular gaps between hollow tube 400 and electrode terminal 58 and to adhesively join electrode terminal 58 to hollow tube 400. Other features of construction are discussed above and shown in FIG. 2E.

In the embodiment shown in FIGS. 2A and 2B, probe 10 includes a return electrode 56 for completing the current path between electrode terminals 58 and power supply 28. Shaft 13 preferably comprises an electrically conducting material, usually metal, which is selected from the group consisting of stainless steel alloys, platinum or its alloys, titanium or its alloys, molybdenum or its alloys, and nickel or its alloys. The return electrode 56 may be composed of the same metal or alloy which forms the electrode terminals 58 to minimize any potential for corrosion or the generation of electrochemical potentials due to the presence of dissimilar metals contained within an electrically conductive fluid 50, such as isotonic saline (discussed in greater detail below).

Figure 2C:
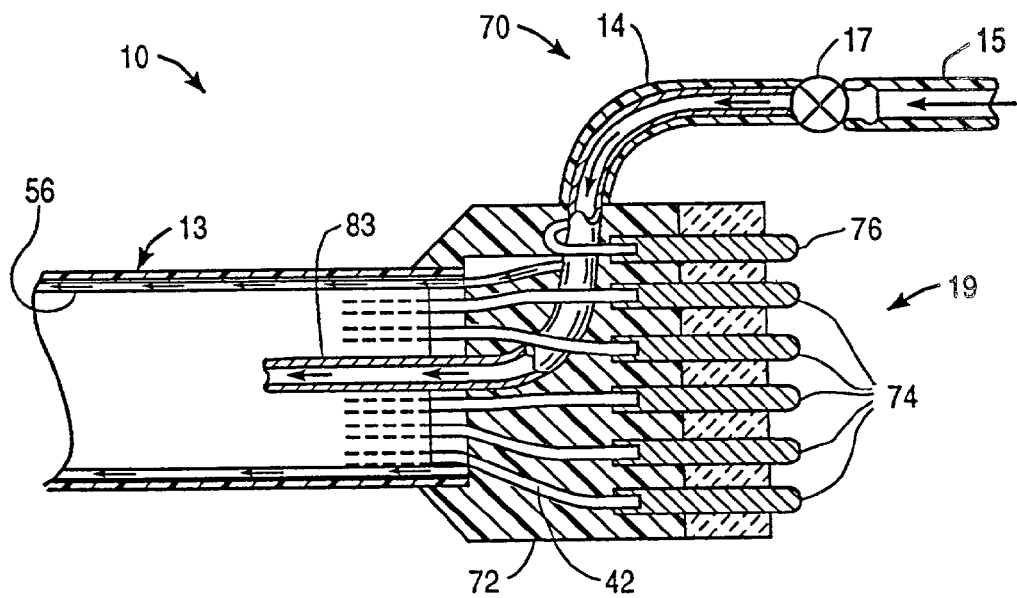
FIG. 2C is a cross-sectional view of the proximal end of the electrosurgical probe of FIG. 2A, illustrating an arrangement for coupling the probe to the electrically conducting liquid supply of FIG. 1.
Figure 2D:
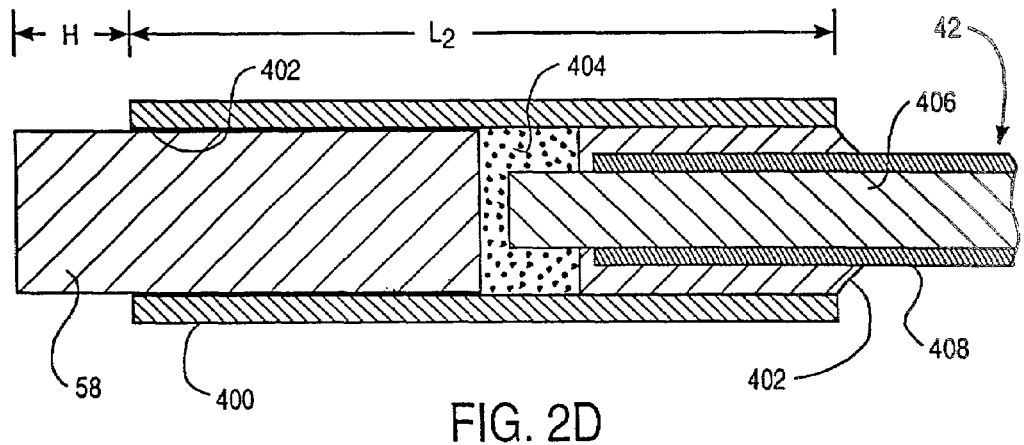
FIGS. 2D and 2E are cross-sectional views of the distal end of the electrosurgical probe of FIG. 2A, illustrating one method of manufacturing the electrode terminals and insulating matrix of the probe.
Figure 2E:
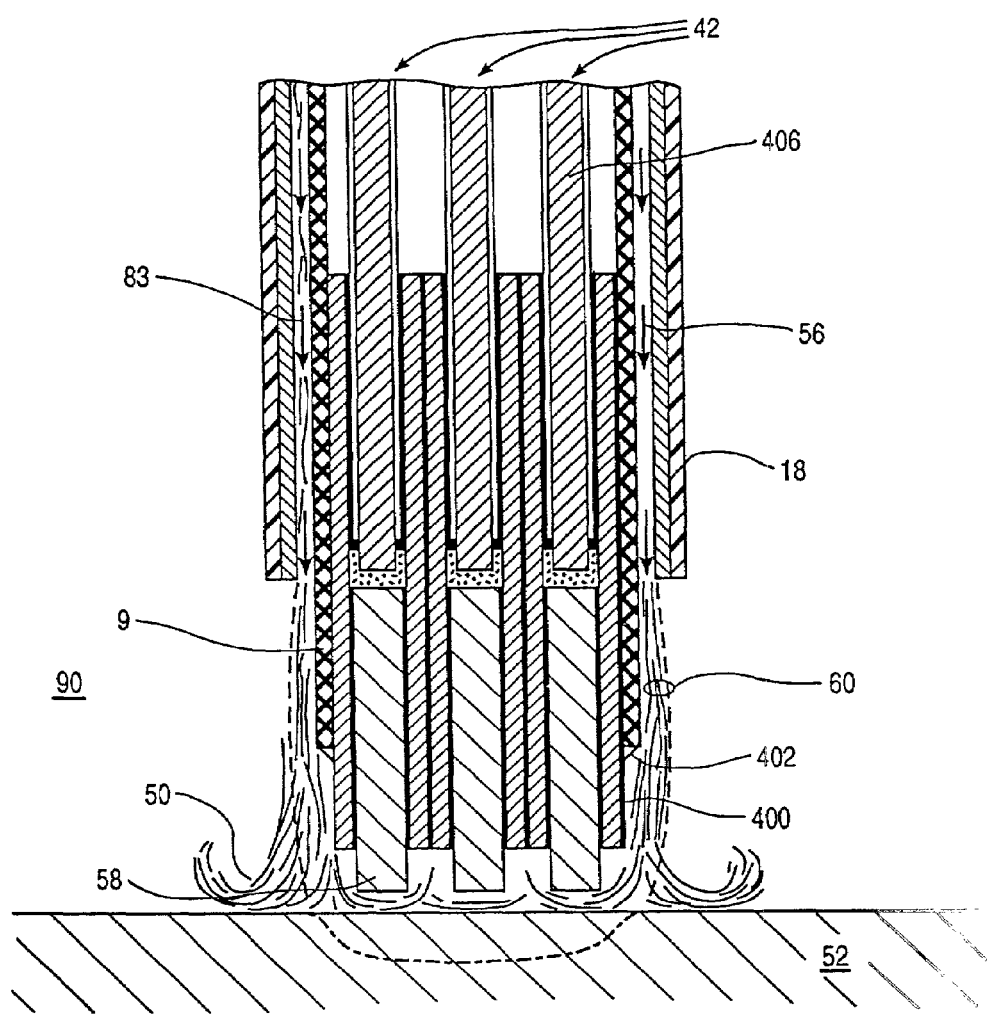

As shown in FIGS. 2A, 2B and 2C, return electrode 56 extends from the proximal end of probe 10, where it is suitably connected to power supply 28 via connectors 19, 20, to a point slightly proximal of electrode array surface 82, typically about 0.5 to 10 mm and more preferably about 1 to 10 mm. Shaft 13 is disposed within an electrically insulative jacket 18, which is typically formed as one or more electrically insulative sheaths or coatings, such as polyester, polytetrafluoroethylene, polyimide, and the like. The provision of the electrically insulative jacket 18 over shaft 13 prevents direct electrical contact between shaft 13 and any adjacent body structure or the surgeon. Such direct electrical contact between a body structure and an exposed return electrode 56 could result in unwanted heating and necrosis of the structure at the point of contact causing necrosis.

In the embodiment shown in FIGS. 2A-2C, return electrode 56 is not directly connected to electrode terminals 58. To complete this current path so that terminals 58 are electrically connected to return electrode 56 via target tissue 52, electrically conducting liquid 50 (e.g., isotonic saline) is caused to flow along liquid paths 83. A liquid path 83 is formed by annular gap 54 between outer return electrode 56 and tubular support member 78. An additional liquid path 83 may be formed between an optional inner lumen 57 within an inner tubular member 59. The electrically conducting liquid 50 flowing through fluid paths 83 provides a pathway for electrical current flow between target tissue 52 and return electrode 56, as illustrated by the current flux lines 60 in FIG. 2A. When a voltage difference is applied between electrode array 12 and return electrode 56, high electric field intensities will be generated at the distal tips of terminals 58 with current flow from array 12 through the target tissue to the return electrode, the high electric field intensities causing ablation of tissue 52 in zone 88.

FIG. 2C illustrates the proximal or connector end 70 of probe 10 in the embodiment of FIGS. 2A and 2B. Connector 19 comprises a plurality of individual connector pins 74 positioned within a housing 72 at the proximal end 70 of probe 10. Electrode terminals 58 and the attached insulating conductors 42 extend proximally to connector pins 74 in connector housing 72. Return electrode 56 extends into housing 72, where it bends radially outward to exit probe 10. As shown in FIG. 1, a liquid supply tube 15 removably couples liquid source 21, (e.g., a bag of electrically conductive fluid elevated above the surgical site or having a pumping device), with return electrode 56. Preferably, an insulating jacket 14 covers the exposed portions of electrode 56. One of the connector pins 76 is electrically connected to return electrode 56 to couple electrode 56 to power supply 28 via cable 34. A manual control valve 17 may also be provided between the proximal end of electrode 56 and supply tube 15 to allow the surgical seam to regulate the flow of electrically conducting liquid 50.

FIGS. 3, 4A and 4B illustrate another preferred embodiment of the present invention. In this embodiment, the probe does not include a fluid channel for directing electrically conducting liquid to the target site. Applicant has found that the fluids in the patient's heart tissue, such as blood, usually have a sufficient amount of electrical conductivity to complete the electrical path between the active electrode array and the return electrodes. In addition, these fluids will often have the requisite properties discussed above for establishing a vapor layer, creating regions of high electric fields around the edges of electrode terminals 58 and inducing the discharge of energetic electrons and photons from the vapor layer to the surface of the target tissue to effect ablation.

As shown in FIG. 3, electrosurgical probe 100 has a shaft 102 with an exposed distal end 104 and a proximal end (not shown) similar to the proximal end shown in FIG. 2C. Aside from exposed distal end 104, which functions as the return electrode in this embodiment, the entire shaft 102 is preferably covered with an electrically insulative jacket 106, which is typically formed as one or more electrically insulative sheaths or coatings, such as polyester, polytetrafluoroethylene, polyimide, and the like, to prevent direct electrical contact between shaft 102 and any adjacent body structure or the surgeon. Similar to the previous embodiment, probe 100 includes an array 108 of active electrode terminals 110 having substantially the same applied potential. Terminals 110 extend from the an insulating inorganic matrix 112 attached to distal end 104 of shaft 102. As discussed above, matrix 112 is only shown schematically in the drawings, and preferably comprises an array of glass or ceramic tubes extending from distal end 104 or is a ceramic spacer through which electrode terminals 110 extend.

The electrode array may have a variety of different configurations other than the one shown in FIGS. 3, 4A and 4B. For example, as shown in FIG. 8, the distal end of the shaft 102 and/or the insulating matrix may have a substantially rectangular shape with rounded corners so as to maximize the perimeter length to cross-sectional area ratio of the distal tip of the probe. As shown, electrode array surface 120 has a rectangular shape having a width in the range of 2 mm to 5 mm and a height in the range of 1 mm to 2 mm. Increasing the perimeter of the artificial channel may have advantages in revascularizing the heart because the blood flowing through the artificial channel will have a greater area to pass into the heart tissue for a given cross-sectional area. Thus, this configuration is a more efficient method of increasing blood flow within the myocardium.

Figure 9:
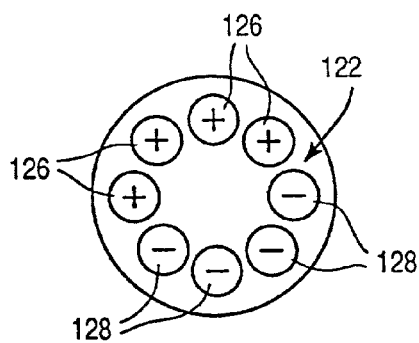
Figure 10:
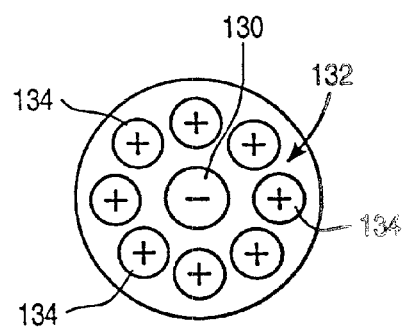
Figure 10A:
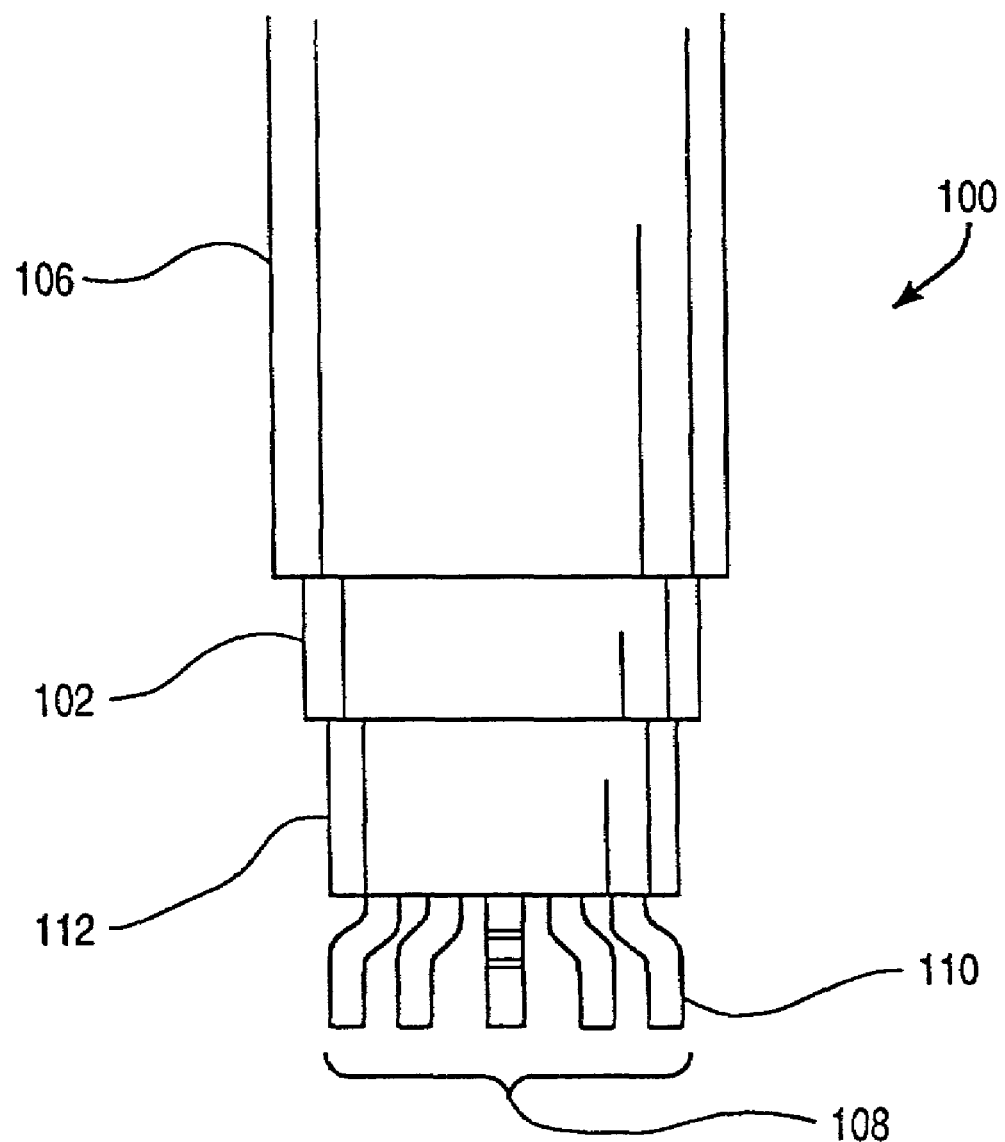

In another embodiment, the return electrode is positioned on the front or distal face of the probe. This configuration inhibits current flow within the tissue on the sides of probe as it forms the revascularizing channel. In one configuration, for example (shown in FIG. 9), the electrode array surface 122 includes multiple pairs of electrodes, with each pair of electrodes including an active electrode 126 and a return electrode 128. Thus, as shown, the high frequency current passes between the pairs across the distal surface 122 of the probe. In another configuration (shown in FIG. 10), the return or common electrode 130 is positioned in the center of the distal probe surface 132 and the active electrodes 134 are positioned at its perimeter. In this embodiment, the electrosurgical current will flow between active electrodes 134 at the perimeter of distal surface 132 and return electrode 130 at its center to form the revascularizing channel. This allows the surgeon to more precisely control the diameter of the revascularizing channel because the current will generally flow radially the outer electrodes 134 and the return electrode 130. For this reason, electrodes 134 will preferably be positioned on the perimeter of distal surface 132 (i.e., further radially outward than shown in FIG. 10A) to avoid tearing of non-ablated heart tissue by the perimeter of the probe shaft.

Figure 6:
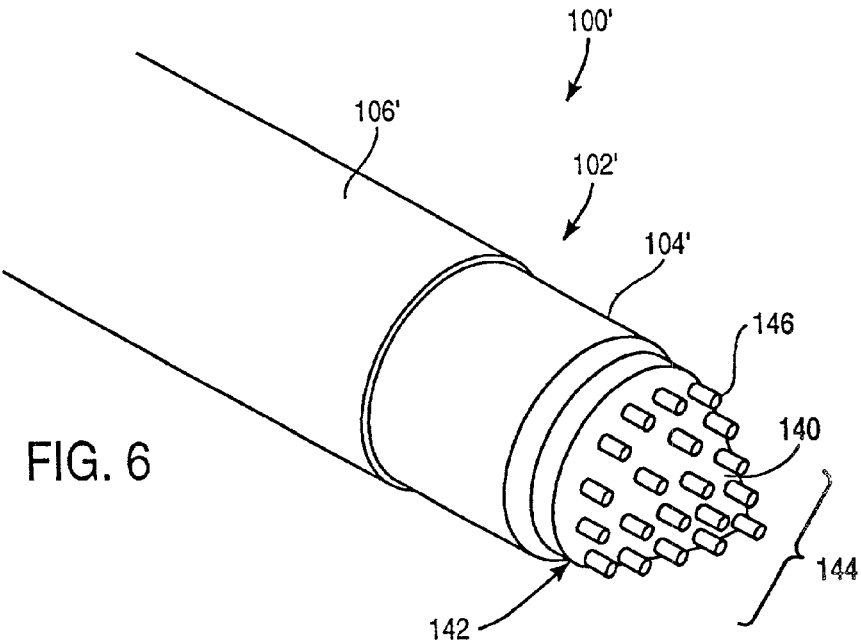
FIGS. 6-10A illustrate alternative electrode arrangements for the probes of FIGS. 1-4 or the catheter of FIG. 5.
Figure 7:
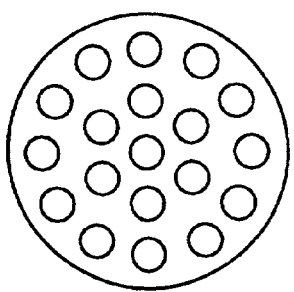

FIG. 6 illustrates yet another embodiment of an electrosurgical probe 100' according to the present invention. In this embodiment, the distal tip of the probe has a conical shape and includes an array of active electrodes along the conical surface 140. A conical shape provides less resistance to the advancement of the probe through dense tissue. As shown in FIG. 6, insulating matrix 142 tapers in the distal direction to form conical distal surface 140. The electrode array 144 extends from distal surface 140, with each electrode terminal 146 arranged to protrude axially from the conical surface 140 (i.e., rather than protruding perpendicularly from the surface 140). With this configuration, the electrodes 146 do not extend radially outward from the conical surface 140, which reduces the risk of electric current flowing radially outward to heart tissue surrounding the revascularizing channel. In addition, the high electric field gradients generated by the electric current concentrate near the active electrode surfaces and taper further away from these surfaces. Therefore, this configuration places these high electric field gradients within the diameter of the desired channel to improve ablation of the channel, while minimizing ablation of tissue outside of the desired channel.

Figure 5:
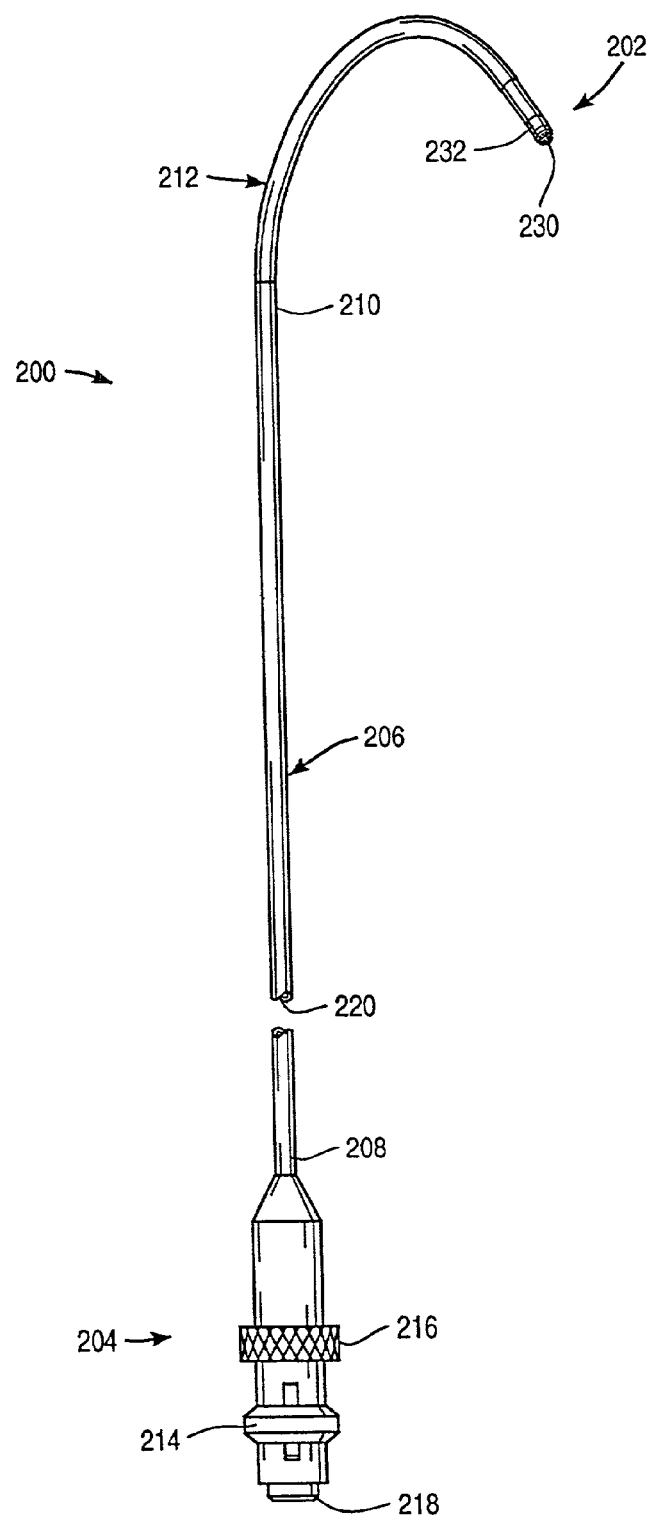
FIG. 5 is a perspective view of a catheter having a shaft with an electrosurgical arrangement at its distal end.

FIG. 5 illustrates a preferred delivery catheter 200 for introducing an electrosurgical probe 202 through a percutaneous penetration in the patient, and endoluminally delivering probe 202 into the ventricle of the heart (this method described in detail below). Catheter 200 generally includes a shaft 206 having a proximal end 208 and a distal end 210. Catheter 200 includes a handle 204 secured to proximal end 208 of shaft, and preferably a deflectable tip 212 coupled to distal end 210 of shaft 206. Probe 202 extends from proximal end, preferably by a distance of about 100 to 200 cm. Handle 204 includes a variety of actuation mechanisms for manipulating tip 212 within the patient's heart, such as a tip actuation slide 214 and a torque ring 216, as well as an electrical connector 218. Catheter shaft 206 will generally define one or more inner lumens 220, and one or more manipulator wires and electrical connections (not shown) extending through the lumens to probe 202.

With reference to FIGS. 11-22, methods for increasing the blood flow to the heart through a transmyocardial revascularization procedure to form artificial channels through the heart wall to perfuse the myocardium will now be described. This procedure is an alternative to coronary artery bypass surgery for treating coronary artery disease. The channels allow oxygen enriched blood flowing into the ventricular cavity to directly flow into the myocardium rather than exiting the heart and then flowing back into the myocardium through the coronary arteries.

Figure 11:
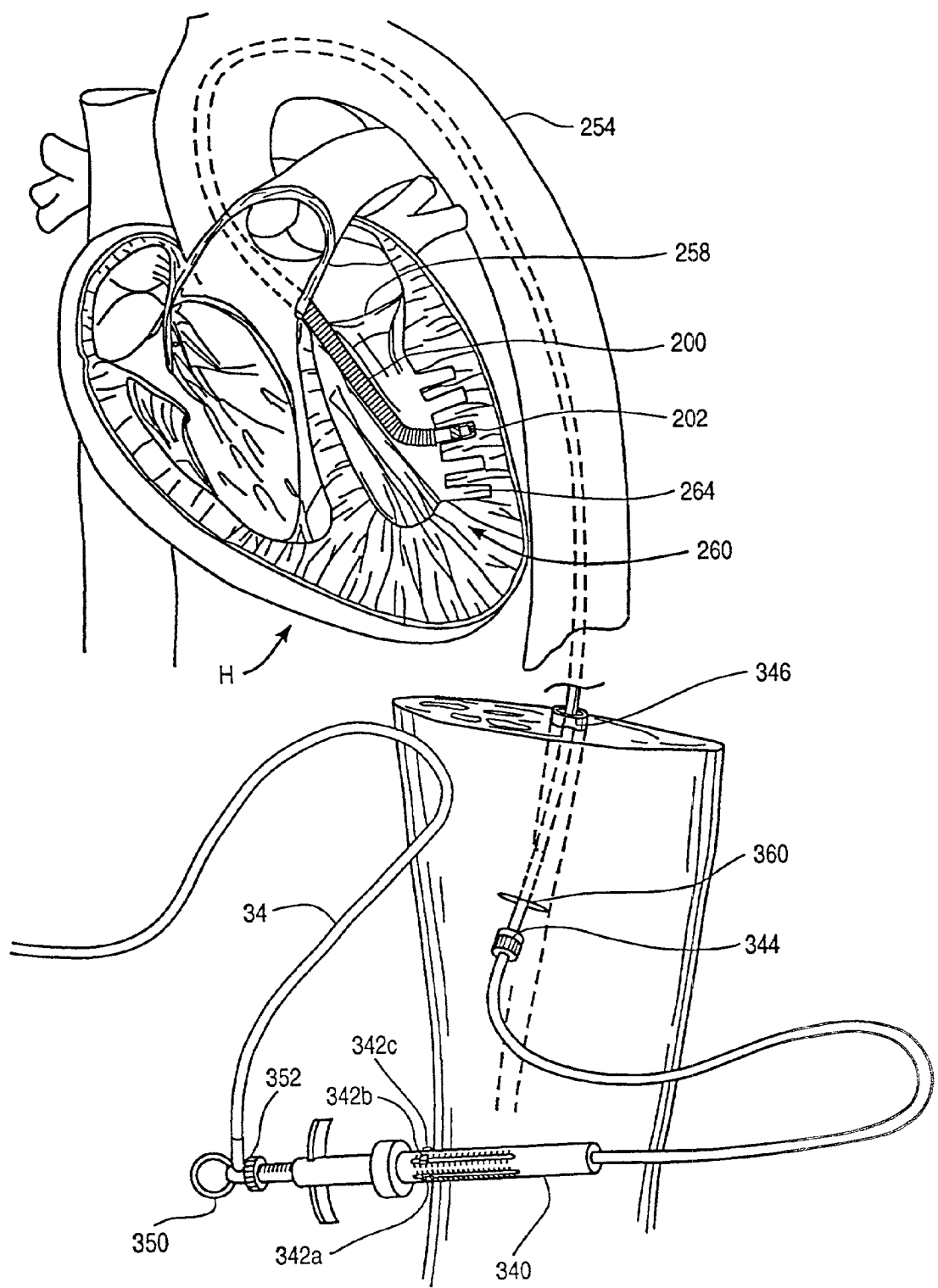
FIG. 11 is a sectional view of the human heart, illustrating the electrosurgical catheter of FIG. 5 within the ventricular cavity for performing a transmyocardial revascularization procedure.

As shown in FIG. 11, electrosurgical probe 202 is positioned into the left ventricular cavity 258 of the heart. Electrosurgical probe 202 may be introduced into the left ventricle 250 in a variety of procedures that are well known in the art, such as a percutaneous, minimally invasive procedures. In the representative embodiment, probe 202 is introduced into the vasculature of the patient through a percutaneous penetration 360 and axially translated via delivery catheter 200 through one of the major vessels, such as the femoral artery 346, through the aorta 254 to the left ventricular cavity 258. A viewing scope (not shown) may also be introduced through a percutaneous position to a position suitable for viewing the target location in the left ventricle 258.

Figure 14:
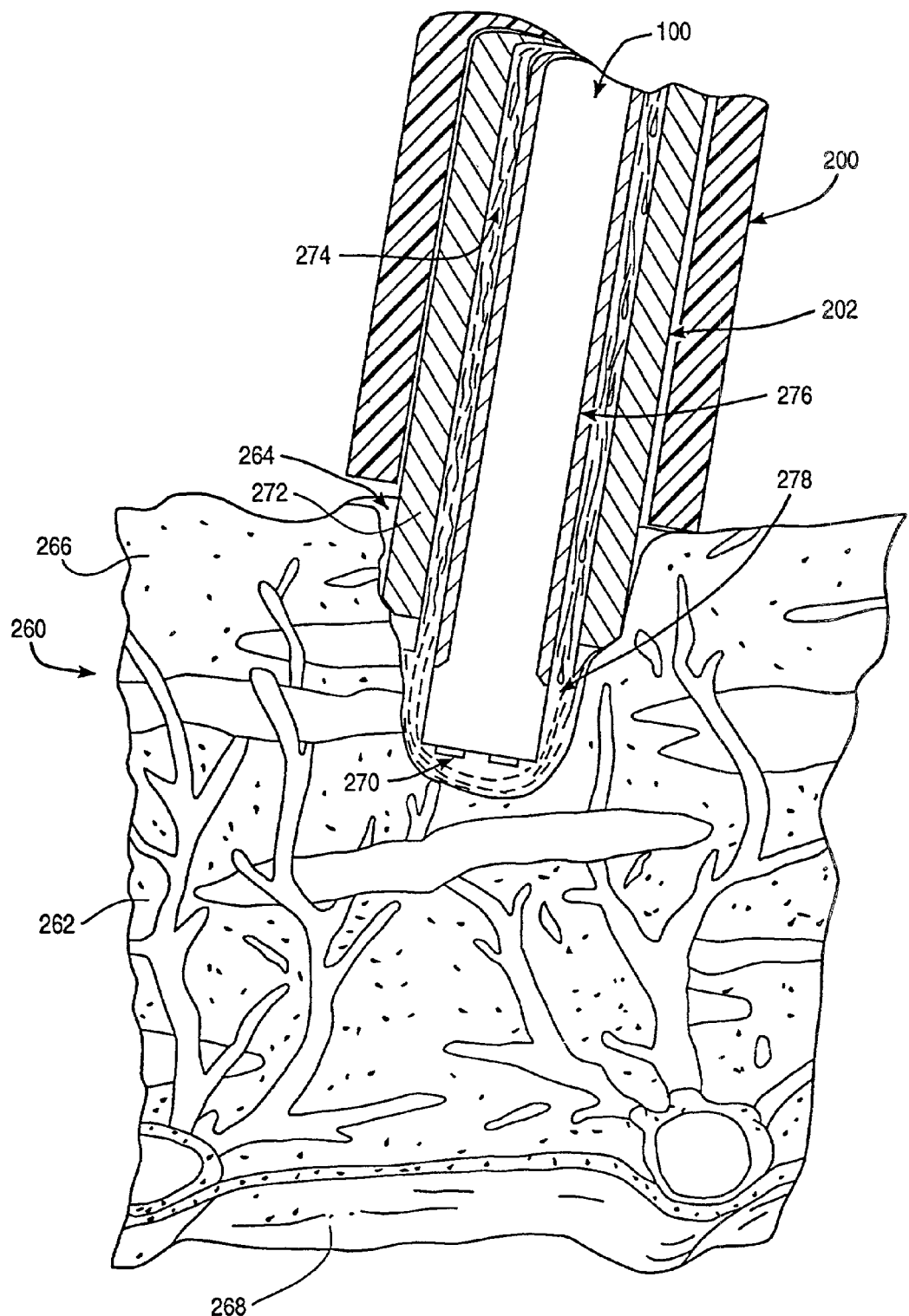
FIG. 14 is a cross-sectional view of the probe of FIG. 1 boring a channel through the myocardium.

Once positioned within the patient's ventricle 258, probe 202 is aligned with the heart wall 260 to form one or more artificial channels 264 for increasing blood flow to the myocardium 262. As shown in FIG. 14, the channels 264 will preferably extend from the endocardium 266 a desired distance through the myocardium 262 without perforating the exterior of the epicardium 268 to inhibit blood from flowing into the thoracic cavity. Preferably, the surgeon will employ a detection or instrument guidance system 350, (discussed below in reference to FIGS. 16, 18, 19 and 20) on probe 202, or another instrument, to determine when the probe is near the outer surface of the epicardium 268. The location of channels 264 may be selected based on familiar endocardial anatomic landmarks. Alternatively, instrument guide system 350 may be used to select target sites on the heart wall, as discussed below.

As shown in FIG. 14, guide catheter 200 is positioned adjacent the inner endocardial wall and probe 202 is axially translated so that the active electrode 270 at its distal end is positioned proximate the heart tissue. In this embodiment, the probe 202 includes a single, annular electrode 270 at its distal tip for ablation of the heart tissue. However, it will be readily recognized that the probe may include an array of electrode terminals as described in detail above. While viewing the region with an endoscope (not shown), voltage can be applied from power supply 28 (see FIG. 1) between active electrode 270 and annular return electrode 272. The boring of channel 264 is achieved by engaging active electrode 270 against the heart tissue or positioning active electrode 270 in close proximity to the heart tissue while simultaneously applying voltage from power supply 28 and axially displacing probe 202 through channel 264. To complete the current path between the active and return electrodes 270, 272, electrically conducting irrigant (e.g., isotonic saline) will preferably be delivered from liquid supply 21 through annular liquid path 274 between return electrode 272 and tubular shaft 200 to the target site. Alternatively, the site may already be submerged in liquid, or the liquid may be delivered through another instrument. The electrically conducting liquid provides a pathway for electrical current flow between the heart tissue and return electrode 272, as illustrated by the current flux lines 278 in FIG. 15.

Figure 15:
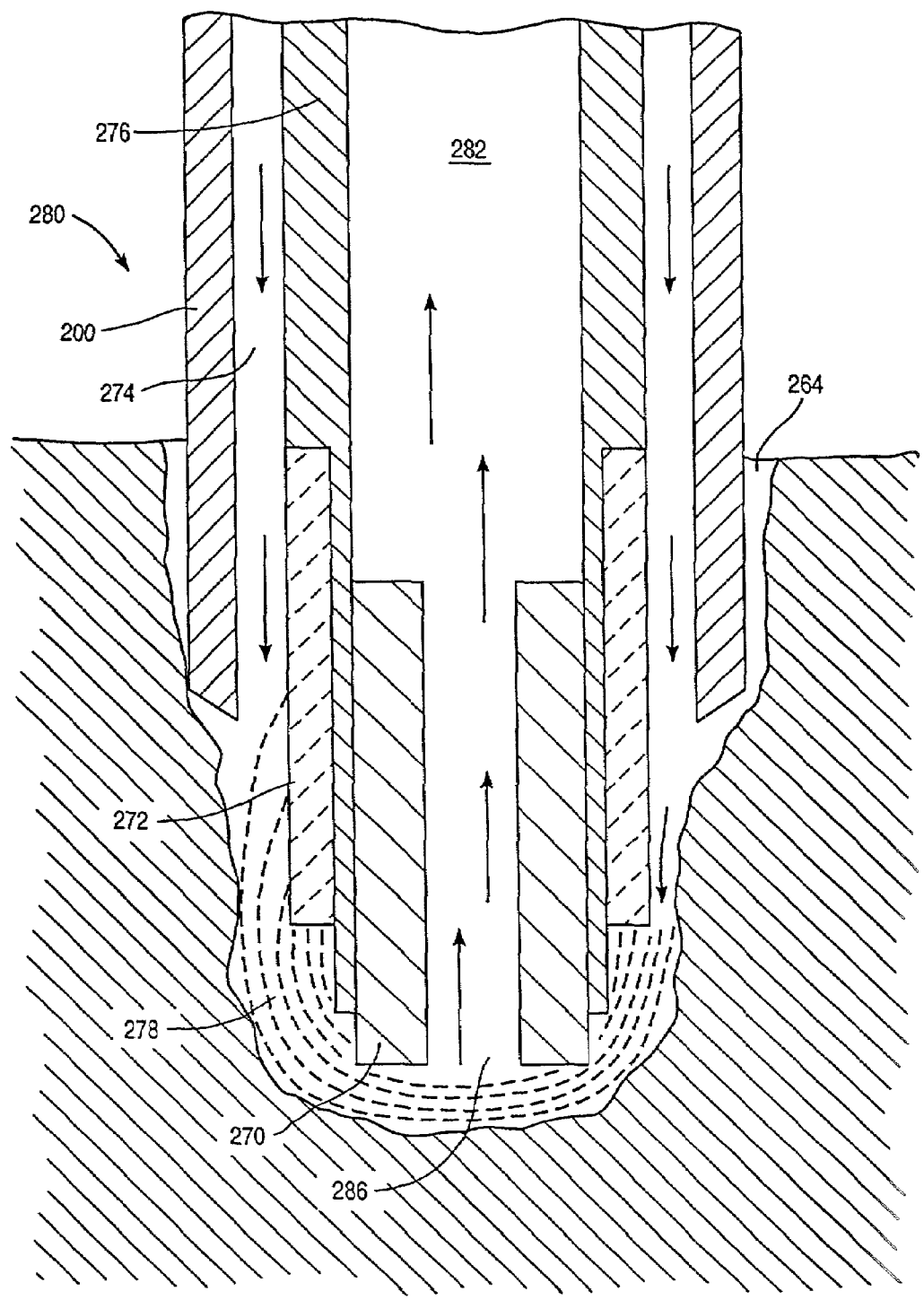
FIG. 15 depicts an alternative embodiment of the probe of FIG. 14 having an outer lumen for delivering electrically conductive liquid to the target site, and an inner lumen for aspirating fluid and gases from the transmyocardial channel.

FIG. 15 illustrates an alternative embodiment of the probe of FIG. 14. In this embodiment, the probe 280 includes a central lumen 282 having a proximal end attached to a suitable vacuum source (not shown) and an open distal end 286 for aspirating the target site. To complete the current path between the active electrode 270 and return electrode 272, electrically conducting irrigant (e.g., isotonic saline) will preferably be delivered from liquid supply 21 (shown in FIG. 1) through annular liquid path 274 between return electrode 272 and tubular shaft 200 to the target site. The active electrode is preferably a single annular electrode 288 surrounding the open distal end 286 of central lumen 282. Central lumen 282 is utilized to remove the ablation products (e.g., liquids and gases) generated at the target site and excess electrically conductive irrigant during the procedure.

Figure 23:
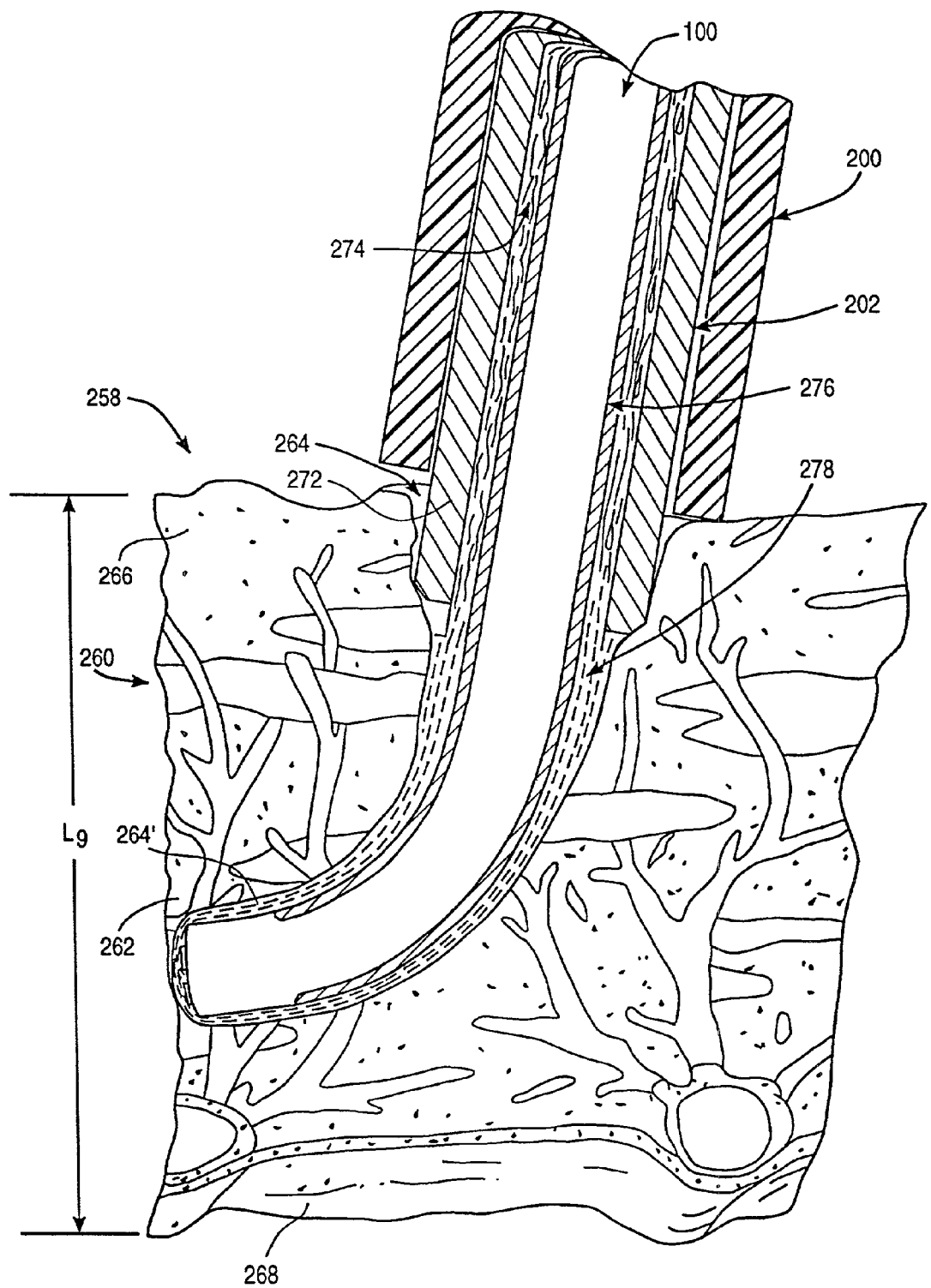
FIG. 23 schematically illustrates a curved revascularizing channel formed by one of the electrosurgical instruments of the present invention.

An alternative embodiment of the percutaneous, endocardial canalization approach is shown in FIG. 23. In this embodiment, electrosurgical catheter 100 can be guided by the surgeon or surgical assistant during the canalization of channel 264 using external handpiece 340 shown in FIG. 11. In this embodiment, the distal portion of the electrosurgical catheter 100 can be caused to follow a curved path to effect a curved artificial channel 264'. By forming a curved artificial channel 264', the total surface area of the artificial channel can be extended so that said channel is longer than the total thickness $L_9$ of the heart wall 260. In addition, by forming a curved artificial channel 264' of proper curvature as shown in FIG. 23, the penetration of the epicardium 268 can be avoided. Still further, the curved artificial channel 264' can be continued forming a complete "U" shaped channel which reenters the ventricular cavity 258 providing one continuous channel which penetrates the endocardium at two locations but does not penetrate through the epicardium 268.

Figure 12:
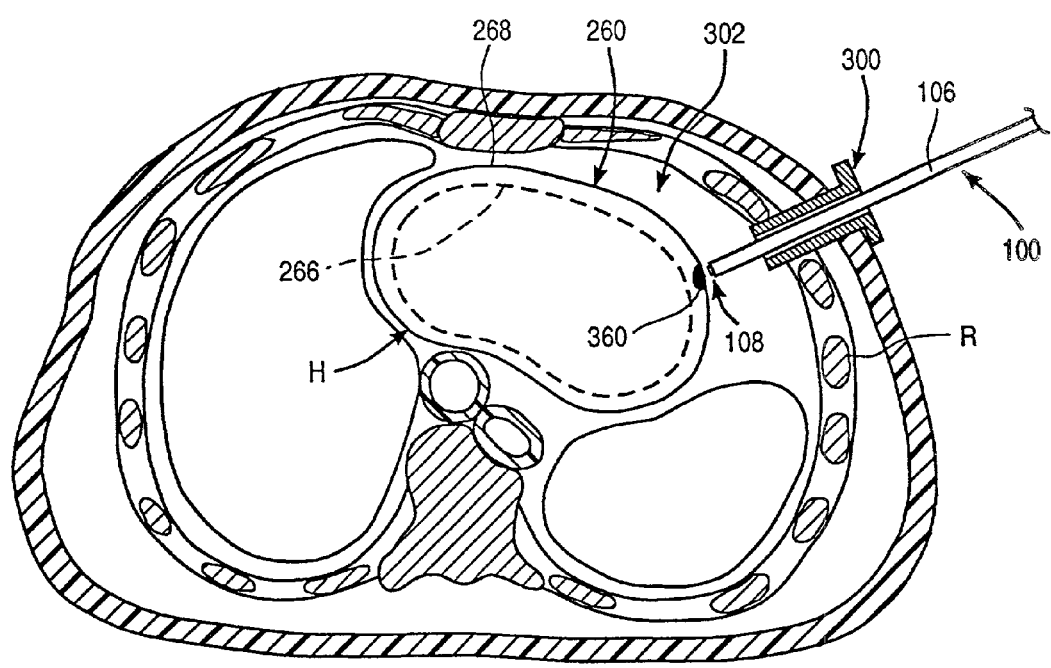
FIG. 12 is a sectional view of the thoracic cavity, illustrating the electrosurgical probe of FIGS. 3, 4A and 4B in a thoracoscopic revascularization procedure.

FIG. 12 illustrates a thoracoscopic procedure for revascularizing the myocardium from the outer wall or epicardium 268 inward to the endocardium 266. At least one intercostal penetration is made in the patient for introduction of electrosurgical probe 100 (FIG. 3) into the thoracic cavity 302. The term "intercostal penetration" as used herein refers to any penetration, in the form of a small cut, incision, hole or cannula, trocar sleeve or the like, through the chest wall between two adjacent ribs which does not require cutting, removing, or significantly displacing or retracting the ribs or sternum. Usually, the intercostal penetration will require a puncture or incision of less than about 5 cm in length. Preferably, the intercostal penetration will be a trocar sleeve 300 having a length in the range from about 2-15 cm, and an internal diameter in the range from 1 to 15 mm, commonly known as thoracic trocars. Suitable trocar sleeves are available from United States Surgical Corp. of Norwalk, Conn., under the brand name "Thoracoport"™. A viewing scope (not shown) may also be introduced through a trocar sleeve to a position suitable for viewing the target location on the heart wall 260. A viewing scope (not shown) may also be introduced through the same or another intercostal penetration into the thoracic cavity 302 to a position suitable for viewing the target location 360 on the surface of the epicardium 268 of the heart. The viewing scope can be a conventional laparoscope or thoracoscope, which typically comprise a rigid elongated tube containing a lens system and an eyepiece or camera mount at the proximal end of the tube. A small video camera is preferably attached to the camera mount and connected to a video monitor to provide a video image of the procedure. This type of scope is commercially available from Baxter Healthcare Corporation of Deerfield, Ill. or United States Surgical Corporation of Norwalk, Conn.

Figure 13:
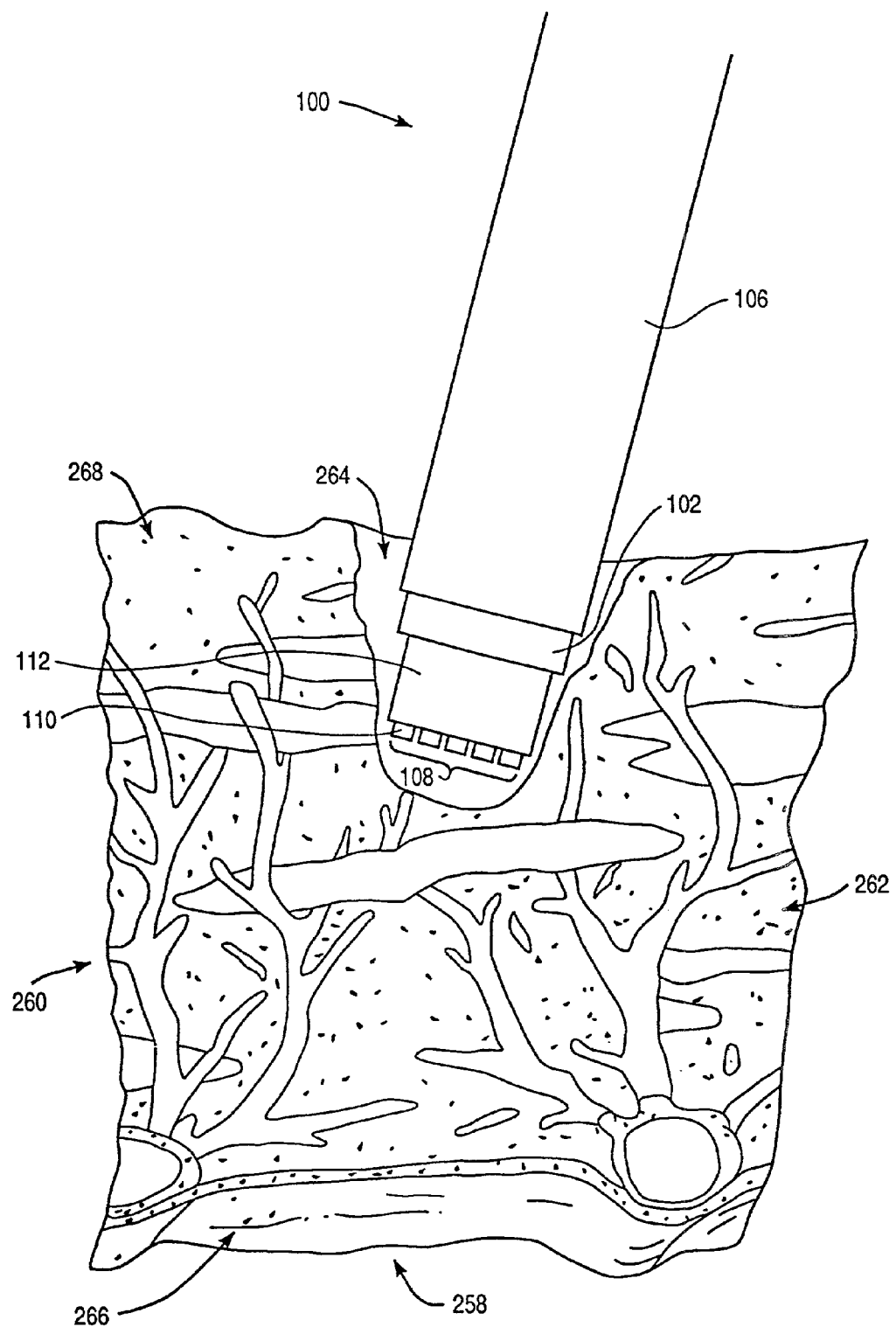
FIG. 13 is a cross-sectional view of the probe of FIGS. 3, 4A and 4B boring a channel through the myocardium.

As shown in FIG. 13, one or more artificial channels 264 are formed by the electrosurgical probe 100 from the outer wall or epicardium 268 through the myocardium 262 and the inner wall or endocardium 266 into the ventricular cavity 258. Similar to the above described method, electrode array 108 is positioned in close proximity to the heart tissue while simultaneously applying voltage from power supply 28 and axially displacing probe 100 through channel 264. In this embodiment, however, electrically conducting liquid is not supplied to the target site to complete the current path between the active electrode terminals 110 and return electrode 102. Applicant has found that the fluids in the patient's heart tissue, such as blood, usually have a sufficient amount of electrical conductivity to complete the electrical path between the active electrode array and the return electrodes. In addition, these fluids will often have the requisite properties discussed above for establishing a vapor layer and inducing the discharge of energetic electrons and photons from the vapor layer to the surface of the target tissue as well as the creation of high electric fields to effect the ablation of tissue.

To inhibit blood from flowing through channels 264 into the thoracic cavity, the channels 264 will preferably be sealed at the epicardium 268 as soon as possible after they have been formed. One method for sealing the artificial channel 264 at the epicardium 268 is to insert a collagen hemostasis device 480 (shown in FIG. 21) using a trocar 300, a cannula 484 and a syringe-like delivery system 486. The collagen, unaffected by antiplatelet or anticoagulant agents that may be present in the patient's blood stream, attracts and activates platelets from the blood 482, rapidly forming a "glue"-like plug near the surface of the epicardium 268 of the newly formed channel 264. Suitable collagen hemostasis devices are available from Datascope Corporation, Montval, N.J. under the brand name "VasoSeal™". The deployment of the collagen hemostasis device 480 is accomplished with the aid of a viewing scope (not shown) which may also be introduced through a trocar sleeve to a position suitable for viewing the target location on the heart wall 260.

To facilitate this sealing procedure, the electrosurgical probe 354 will preferably include a guidance system 350 (FIG. 16) for determining when the probe is close to the inner surface of the endocardium 266 so that the surgeon can prepare to withdraw probe 100 and seal the channel 264.

In both of the above embodiments, the present invention provides localized ablation or disintegration of heart tissue to form a revascularization channel 264 of controlled diameter and depth. Usually, the diameter will be in the range of 0.5 mm to 3 mm, preferably between about 1 to 2 mm. Preferably, the radio frequency voltage will be in the range of 300 to 2400 volts peak-to-peak to provide controlled rates of tissue ablation and hemostasis while minimizing the depth of necrosis of tissue surrounding the desired channel. This voltage will typically be applied continuously throughout the procedure until the desired length of the channel 264 is completely formed.

However, the heartbeat may be monitored and the voltage applied in pulses that are suitably timed with the contractions (systole) of the heart.

Ablation of the tissue may be facilitated by axially reciprocating and/or rotating the electrosurgical probe a distance of between about 1 to 5 mm. This axial reciprocation or rotation allows the electrically conducting liquid (FIG. 14) to flow over the tissue surface being canalized, thereby cooling this tissue and preventing significant thermal damage to the surrounding tissue cells.

Figure 16:
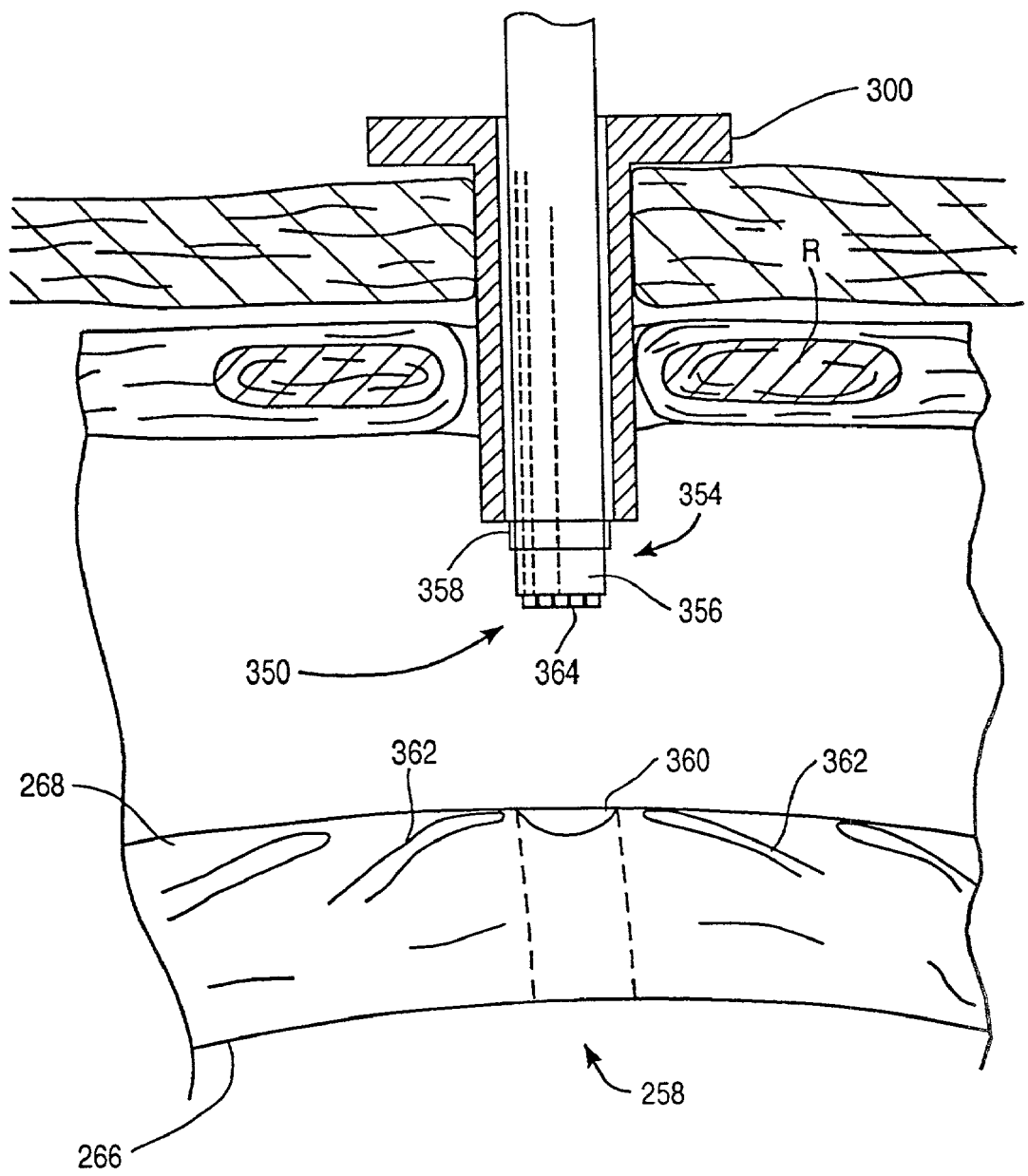
FIG. 16 is a side view of an electrosurgical probe incorporating a fiberoptic viewing device and a light generator for sighting the probe onto a target site on the heart tissue.

FIG. 16 illustrates one representative guidance system 350 for guiding an electrosurgical probe 354 to target sites on the heart wall. Guidance system 350 is provided for detecting an "end point" for each artificial channel and/or for determining appropriate target sites on the heart wall for forming the artificial channels. The instrument guidance system 350 will preferably allow a surgeon to determine when the electrosurgical probe 354 (or an electrosurgical catheter) is near the other end of the heart wall (i.e., the outer edge of the epicardium or the inner edge of the endocardium). The guidance system 350 indicates to the surgeon to stop axially translating the probe 354 so that the probe does not form a channel completely through a heart wall, which limits bleeding and/or reduces damage to surrounding tissue structures or blood. Alternatively or in addition, the guidance system 354 will allow the surgeon to determine an appropriate target site 360 on the heart wall to form the channel to avoid accidental puncturing of relatively large vessels in the heart wall.

In one embodiment shown in FIG. 16, the instrument guidance system 350 includes a fiberoptic viewing cable 356 within electrosurgical probe 354, and a visible light generator 358, such as a laser beam, integral with the probe for illuminating a target site 360 on the heart wall. Note that both light generator 358 and fiberoptic cable 356 may be coupled to an instrument other than probe 354. The fiberoptic viewing cable 356 sites the target site 360 illuminated by the visible light generator 358 to locate where the probe 354 will bore the hole. This allows the surgeon to avoid puncturing larger blood vessels 362 on the heart wall (e.g., coronary arteries or veins). Visible light generator 358 may also be used to determine when the distal end 364 of probe 354 is close to the opposite side of the heart wall, or when the probe 354 has completely penetrated through the heart wall into the ventricular cavity 258.

In a second embodiment, the detection system is an ultrasound guidance system that transmits sound waves onto the heart wall to facilitate canalization of the heart.

Figure 18:
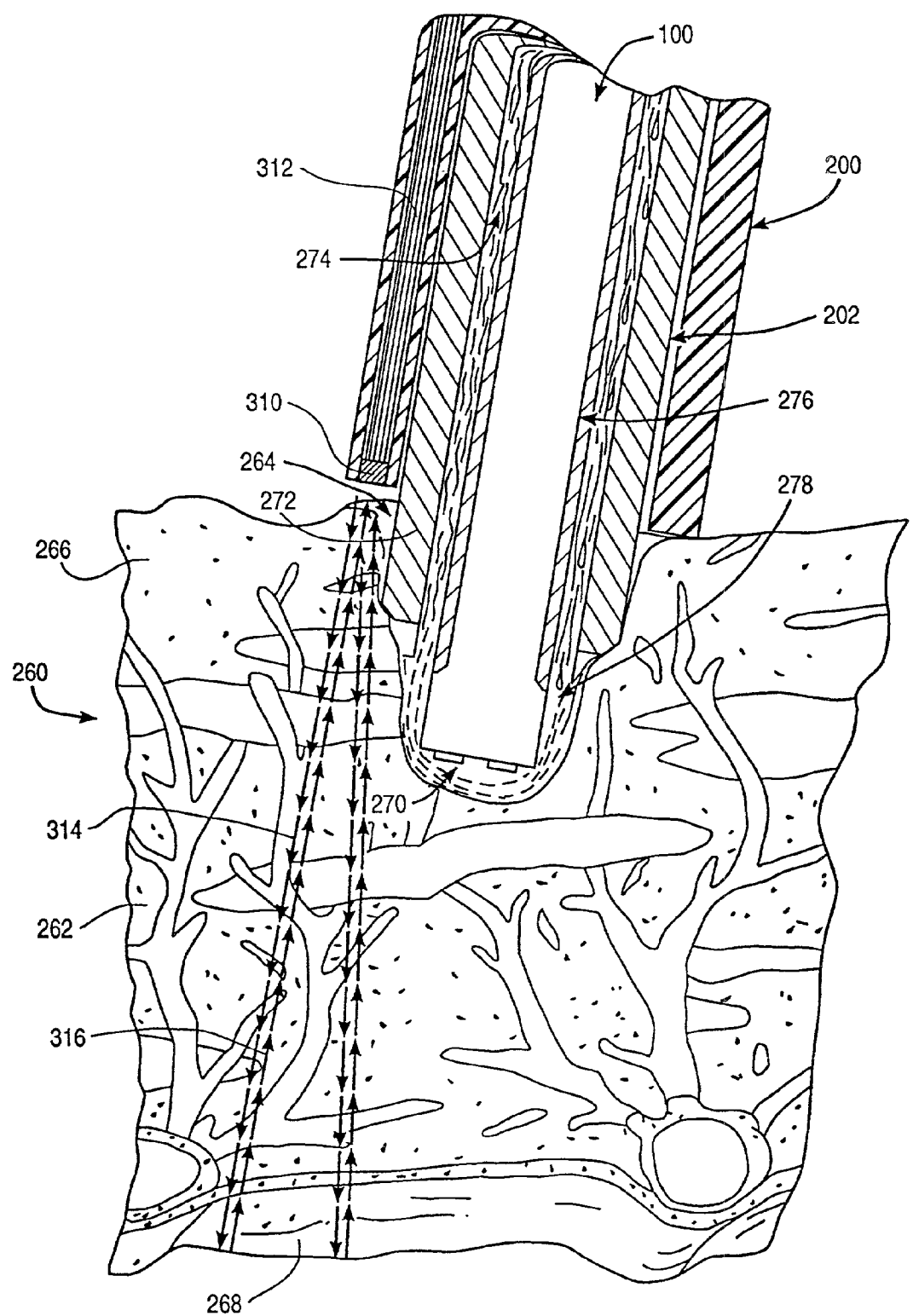
FIG. 18 is a cross-sectional view of the probe of FIG. 1 boring a channel into the myocardium with an ultrasound tissue thickness measuring device located on a guide catheter.
Figure 19:
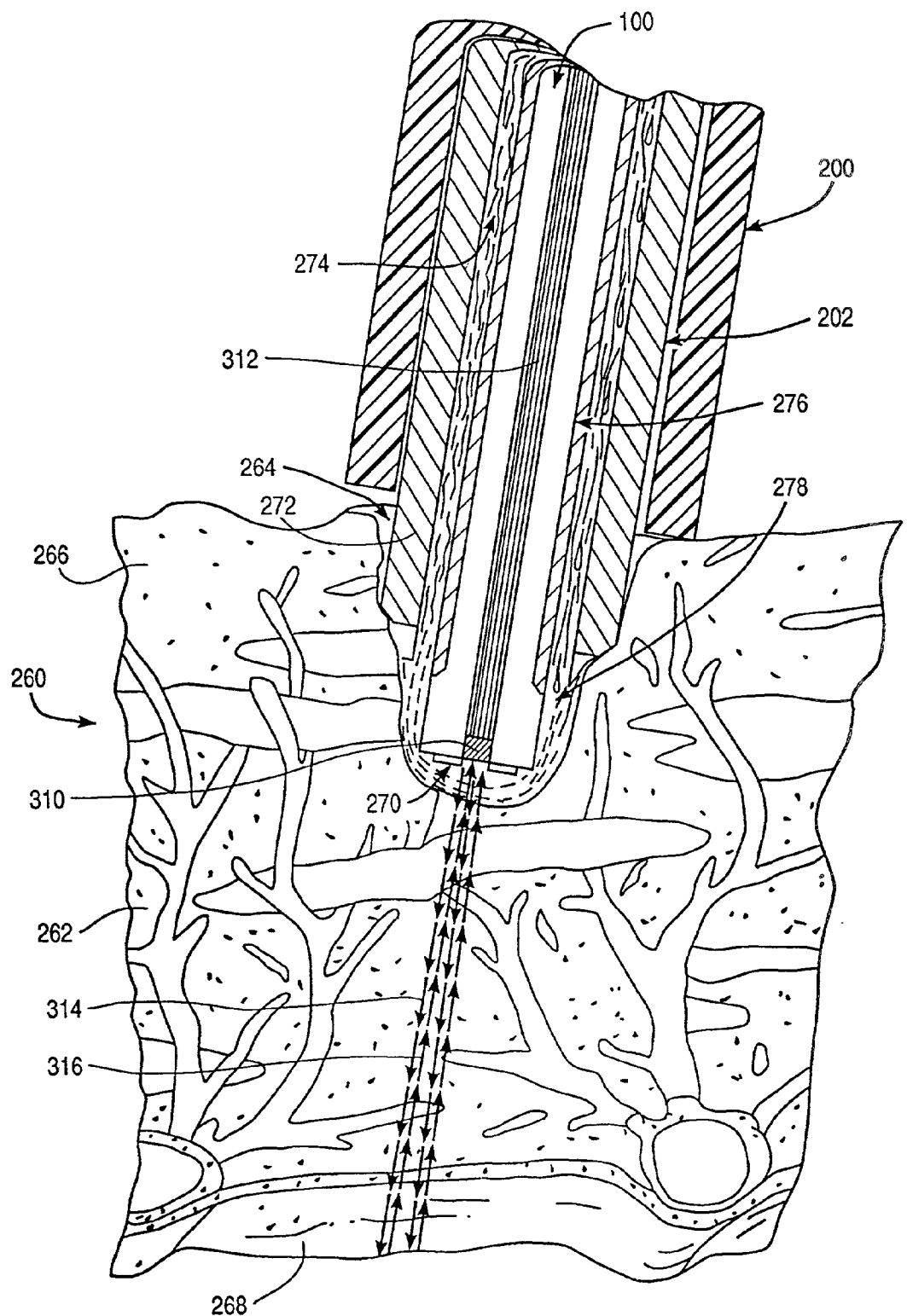
FIG. 19 is a cross-sectional view of the probe of FIG. 1 boring a channel into the myocardium with an ultrasound tissue thickness measuring device located on an electrosurgical catheter.

Referring to FIGS. 18 and 19, an ultrasound tissue thickness measuring system may be incorporated within the electrosurgical catheter 100 or guide tube 200 to measure the thickness of the heart wall 260 adjacent to the distal probe tip 270 and thereby allow the surgeon to pre-set the depth of each channel using adjustable stop 352 on handpiece 340 (FIG. 11) before energizing the electrosurgical catheter 100 and ablating the heart tissue. In the embodiment shown in FIG. 18, an ultrasonic transducer 310 affixed to the distal end of guide tube 200 and connected to an external ultrasonic generator and sensing system (not shown) via lead 312, transmits pulses of ultrasound into the heart tissue in the form of emitted ultrasound signal 314 and the ultrasound generator and sensing system measures the delay time for reflected ultrasound signal 316 to return from the boundary of the heart wall at the surface of epicardium 268. This delay time can be translated into a thickness of the entire heart wall and allow the surgeon to adjust the maximum travel distance of electrosurgical catheter 100 using mechanical stop 352 (FIG. 11) to prevent the length of channel 264 from extending through the outer surface of the epicardium 268. The surgeon can choose to stop the canalization of the heart at any selected distance of the epicardium which may typically be in the range from about 1 mm to 10 mm.

A third embodiment is shown in FIG. 19 wherein an ultrasonic transducer 310 is affixed to the distal end of electrosurgical catheter 100 and connected to an external ultrasonic generator and sensing system (not shown) via leads 312, and transmits pulses of ultrasound into the heart tissue in the form of emitted ultrasound signal 314. The ultrasound generator and sensing system measures the delay time for reflected ultrasound signal 316 to return from the boundary of the heart wall at the surface of epicardium 268. This measured delay time can be translated into the distance between the distal tip 270 of electrosurgical catheter 100 and the surface of the epicardium 268. In this arrangement, the surgeon can observe where the channel 264 reaches the preferred distance from the epicardium 268 and interrupt the application of power and advancement of electrosurgical catheter 100. Alternatively, the preferred minimum thickness of the uncanalized heart wall 260 (i.e., the minimum distance from the bottom of channel 264 to the surface of the epicardium 268) can be preselected by the surgeon. When this distance is reached based on the thickness of the uncanalized heart wall measured using the ultrasonic generator and sensor system (now shown), the ultrasonic generator and sensor system provides an electrical signal to the power source for the electrosurgical catheter 100 to interrupt the applied voltage, thereby ending the canalization process and limiting the depth of channel formed. In this manner, the surgeon may hear an audible tone and will "feel" the catheter advancement stop at the moment the applied voltage is interrupted.

Figure 20:
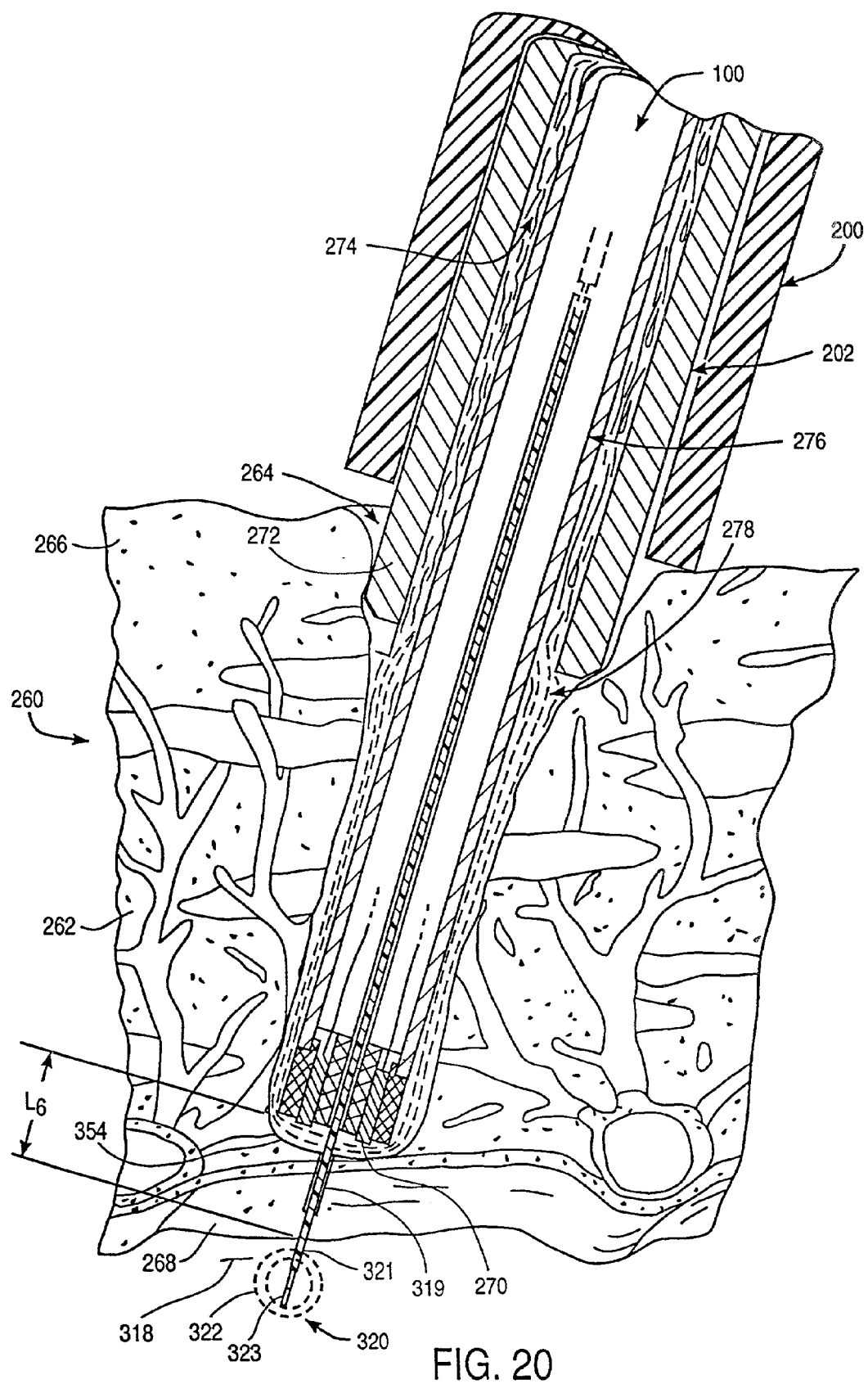
FIG. 20 is a cross-sectional view of the probe of FIG. 1 boring a channel into the myocardium with an electrical impedance sensor located on an electrosurgical catheter to detect crossing through a surface of the heart at a distance $L_1$ distal to the electrode array.

A fourth embodiment is shown in FIG. 20 in which electrosurgical catheter 100 includes a small diameter tissue electrical impedance measurement sensor 319 which extends distal to the tissue ablating electrode array 270 by a distance $L_6$. The impedance measurement sensor 319 detects the outer surface of the epicardium 268 as it enters a region of different electrical impedance (viz, the fluid-filled cavity surrounding the heart). In the present embodiment, sensor tip 320 may include a first impedance measurement electrode 321 and a second impedance measurement electrode 323. A small, high-frequency potential is applied between first and second impedance measurement electrodes 321 and 323 causing current flow between first and second impedance measurement electrodes 321 and 323 as indicated by current flux lines 322. As the first and second electrodes 321 and 323 emerge from the epicardium 268 into cavity 318 surrounding the heart, the change in the electrical impedance is measured and may be indicated by an audible signal and/or may be used as a direct feedback control signal to interrupt the application of voltage to the electrosurgical catheter 100 by generator 28 (FIG. 1). By this method, the forward advancement of the electrosurgical catheter 100 can be limited to a preselected distance $L_6$ between the bottom of channel 264 and the surface of the epicardium 268.

In a fifth embodiment shown in FIG. 13, the guidance system utilizes impedance measurement circuitry integrated with the ablating electrodes 110 to detect when the electrosurgical catheter probe 100 is adjacent blood vessels and/or the outer or inner boundaries of the heart wall. Specifically, the current limiting circuitry includes a number of impedance monitors coupled to each electrode terminal to determine the impedance between the individual electrode terminal 110 and the return of common electrode 102. Thus, for example, if the measured impedance suddenly decreases at electrode terminals 110 at the tip of the probe 100, the applied voltage will be interrupted to avoid power delivery to blood filled ventricular cavity 258 of the heart, thereby avoiding formation of a thrombus or damage to other tissue structures within the ventricular cavity 258.

Figure 17:
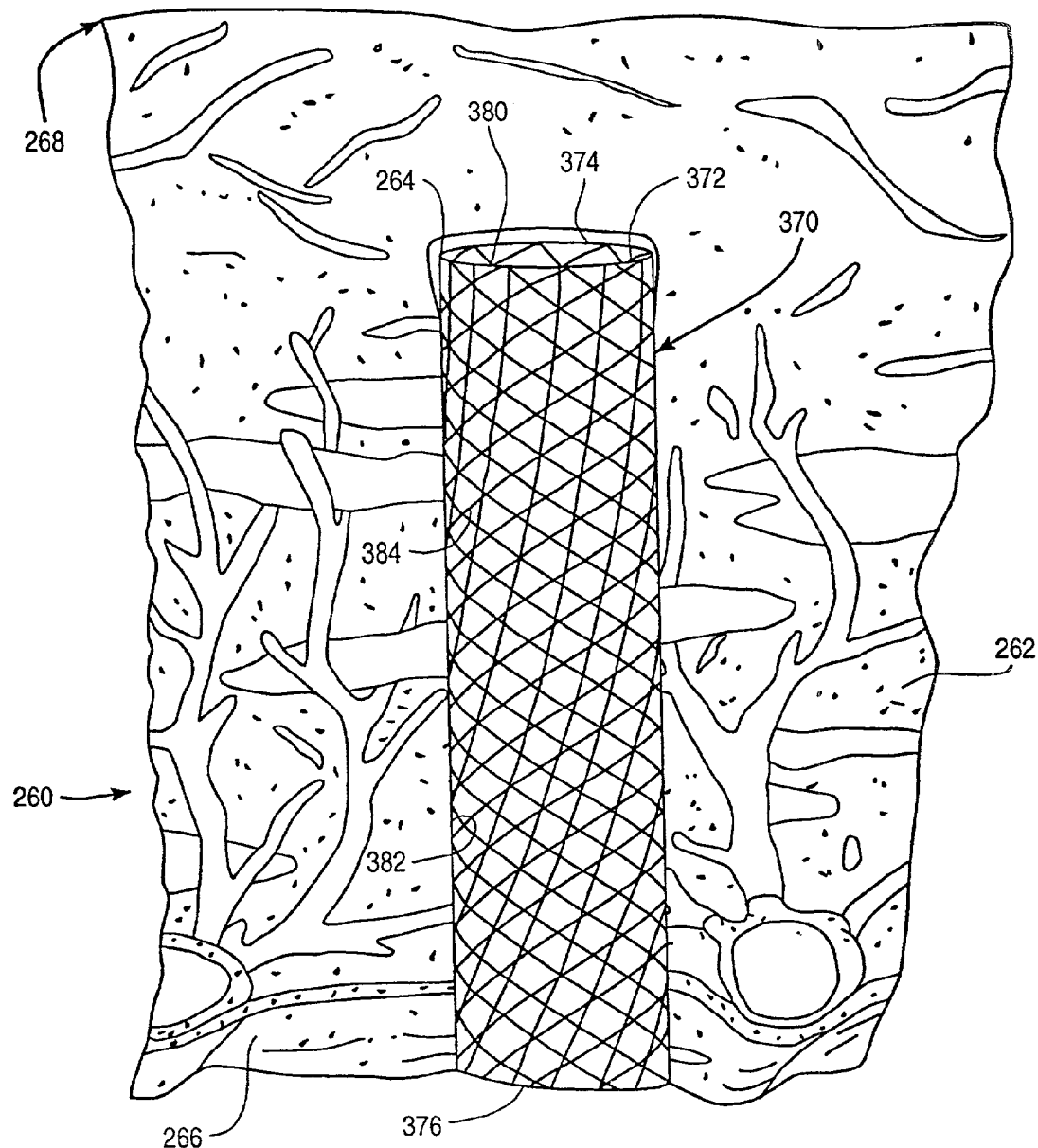
FIG. 17 schematically illustrates a lumenal prosthesis positioned in a revascularizing channel during a percutaneous procedure to maintain lumen patency.

FIG. 17 illustrates a method for implanting a luminal prosthesis, such as a stent or stent-graft 370, into the artificial channels 264 formed by one of the electrosurgical probes or catheters of the present invention to maintain the patency of these channels 264. The stents 370 are usually compressed into a narrow-diameter configuration (not shown), and advanced endoluminally to one of the artificial channels 264 in the heart wall with a conventional or specialized delivery catheter (not shown). Alternatively, the electrosurgical probe may be designed to delivery and implant the stents 370 at the target site. The stents 370 will typically comprise a resilient, radially compressible, tubular frame 372 having a proximal end 374, a distal end 376, and an axial lumen 380 therebetween. The tubular frame 372 includes a plurality of openings or slots (not shown) that allow it to be expanded radially outward into the enlarged configuration shown in FIG. 17 by conventional methods, such as shape memory alloys, expandable balloons, and the like. The stent 370 exerts a radial force against the inner channel walls 382 to maintain lumen patency and/or mechanically augment luminal wall strength, thereby maintaining the blood flow from the ventricular cavity to the myocardium. The stent 370 may also include a graft or liner 384 for inhibiting cell proliferation and occlusion through the openings and slots of frame 372.

In a first embodiment shown in FIG. 17, the stent 370 is introduced into the artificial channel 264 during a percutaneous procedure as illustrated in FIG. 11. In this embodiment, the length of each channel 264 and hence the length of each stent 370 extends only partially through the entire thickness of heart wall 260.

Figure 21:
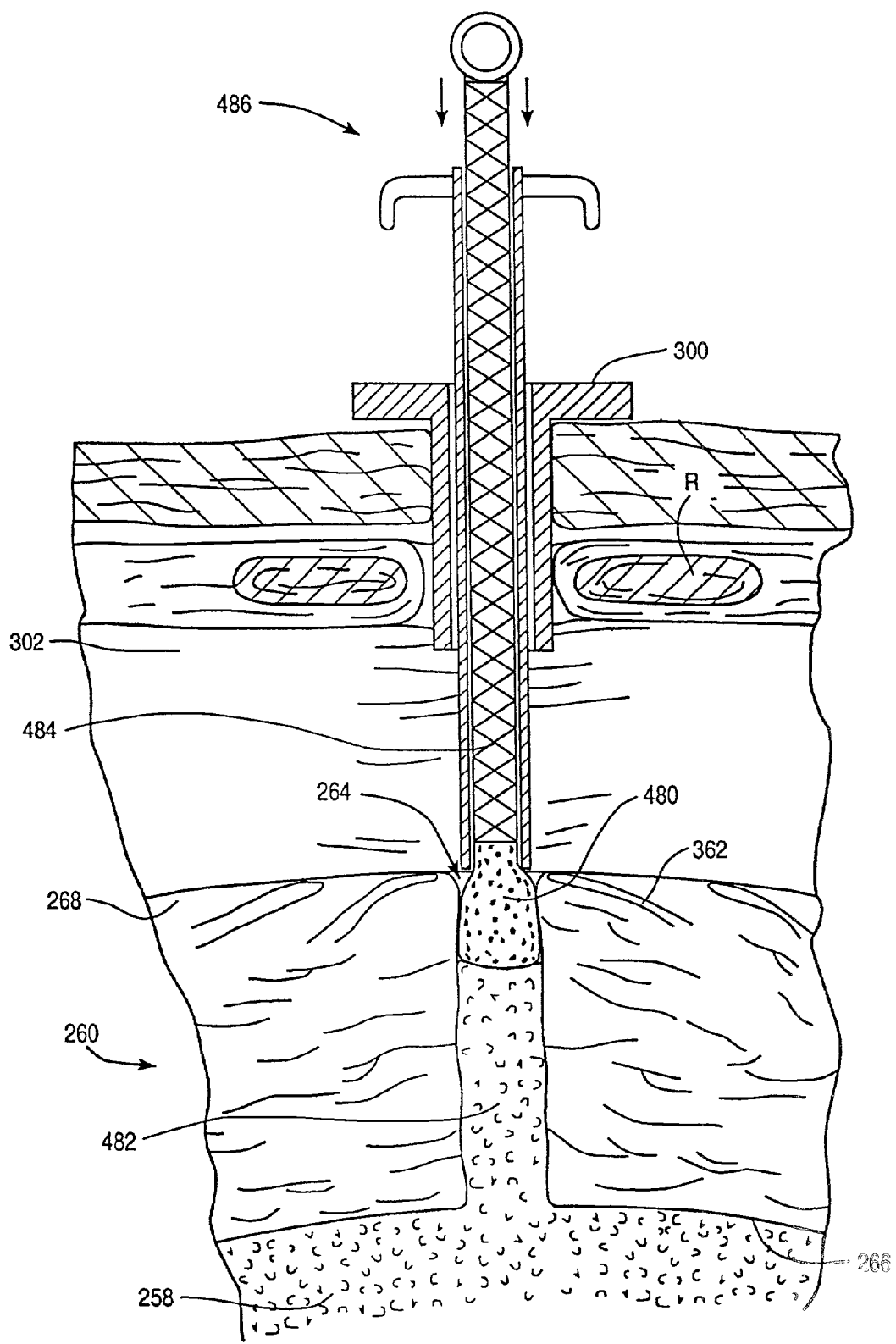
FIG. 21 is a schematic cross-sectional view of a hemostasis device for sealing artificial revascularizing channels formed by one of the electrosurgical instruments of the present invention.
Figure 22:
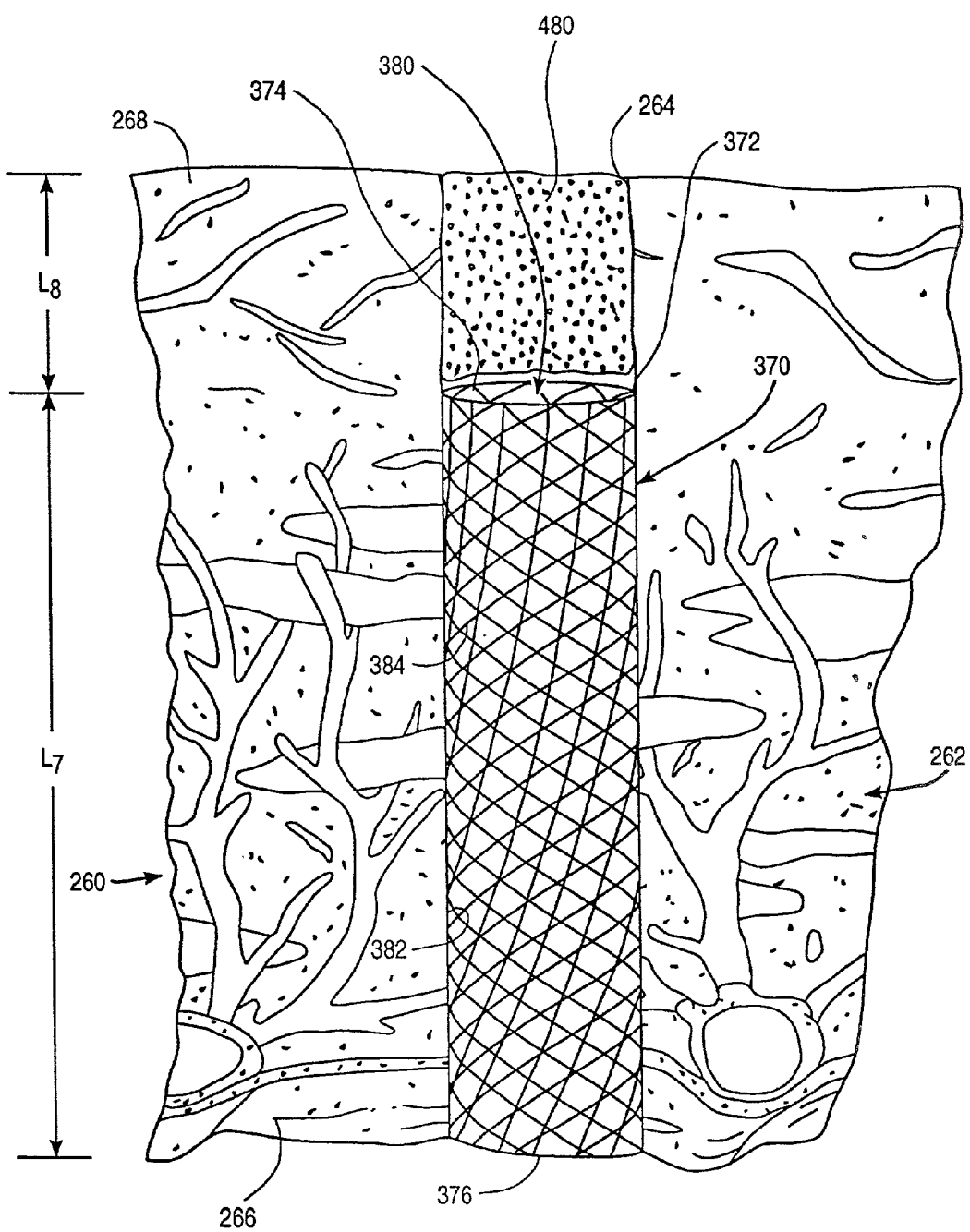
FIG. 22 is schematically illustrates a lumenal prosthesis positioned in a revascularizing channel during a thoracoscopic procedure to maintain lumen patency.

In a second embodiment shown in FIG. 22, the stent is introduced into the artificial channel 264 during a thoracoscopic procedure as illustrated in FIG. 12. In this embodiment, the length of each artificial channel 264 extends completely through the heart wall 260 to allow the blood within the ventricular cavity 258 to circulate within the majority of the length of the artificial channel 264. However, in this embodiment, the stent 370 is placed in the distal portion of the artificial channel 264 as shown in FIG. 22 extending to the endocardium 266 to maintain patency of the artificial channel 264 over length $L_7$ of heart wall 260. Following insertion and deployment of stent 370, the proximal portion of artificial channel 264 may be sealed using collagen hemostasis device 480, or the like, as described hereinbefore related to FIG. 21 using a cannula 484 and syringe-like delivery system 486 as shown in FIG. 21. The collagen hemostasis device 480 attracts and activates platelets from the blood 482, rapidly forming a "glue"-like plug near the surface of the epicardium 268 of the newly formed artificial channel 264. Alternatively, a collagen hemostasis device may be deployed through a central lumen 59 integral with the electrosurgical probe or catheter as illustrated in FIG. 2A. The collagen hemostasis device can be compressed to fit within a lumen 59 whose diameter is smaller than that of the artificial channel 264. When ejected form the confining lumen 59, the collagen hemostasis device 480 expands to fill the full diameter of the artificial channel 264 over length $L_8$ as shown in FIG. 22. Also, such a system for the deployment of a collagen hemostasis device 480 or the like may be integrated with the electrosurgical catheter 100 used for the percutaneous canalization of artificial channels 264 according to method illustrated in FIG. 11. Referring to FIGS. 2A, 11 and 22, in a percutaneous approach using this sealing method, the artificial channel 264 would be formed through the entire thickness of the heart wall 260. Once the surface of the epicardium 268 is penetrated, the position of the tip 202 of the electrosurgical catheter 100 is retracted a distance $L_8$. Next, a collagen hemostasis device 480 or the like is deployed from the central lumen 59 of electrosurgical catheter 100. When ejected from the confining lumen 59, collagen hemostasis device 480 expands to fill the full diameter of the artificial channel 264 over length $L_8$ as shown in FIG. 22 to effect a seal to prevent blood loss through the opening in the epicardium 268. Alternatively, suturing techniques may be employed, either percutaneously, thoracoscopically or in an open chest procedure to seal the opening of the artificial channels at the surface of the epicardium 268.

The stent frame 372 of the present invention is typically manufactured from a tubular material, such as tubing made out of shape memory alloy having elastic or pseudo-elastic properties, such as Nitinol™, Elgiloy™, or the like. Alternatively, the stent frame may comprise malleable materials other than shape memory alloys, such as stainless steel. In this configuration, the stent frames will preferably be expanded at the target site by conventional methods, e.g., an expandable balloon at the distal end of a catheter shaft. The tubular member is usually significantly smaller in diameter as compared to the final diameter of the stent in the expanded configuration within the body lumen. Slots may be cut into the tubes via laser cutting methods, photo etching, or other conventional methods to form the separate stent frames. For example, these methods include coating the external surface of a tube with photoresist material, optically exposing the etch pattern using a laser beam while translating and rotating the part, and then chemically etching the desired slot pattern of the state using conventional techniques. A description of this technique can be found in U.S. Pat. No. 5,421,955 to Lau, the complete disclosure which is incorporated herein by reference. In other methods, laser cutting technology is used in conjunction with computer controlled stages to directly cut a pattern of slots in the wall of the hypodermic tubing to obtain the desired stent geometry. A description of a typical laser cutting method is disclosed in U.S. Pat. No. 5,345,057 to Muller, the complete disclosure of which is incorporated herein by reference.

In an exemplary configuration, the stent frame 372 is formed from a resilient shape memory alloy material that is capable of being deformed by an applied stress, and then recovering to its original unstressed shape. The alloy material will usually exhibit thermoelastic behavior so that the stents will transform to the original unstressed state upon the application of heat (i.e., an $A_f$ temperature below body temperature). The stents may also exhibit stress-induced martensite, in which the martensite state is unstable and the prosthesis transforms back to the original state when a constraint has been moved (i.e., when the stent is released from an introducing catheter within a body lumen). The material for the shape memory alloy will be selected according to the characteristics desired of the population of prostheses. Preferably, the shape memory alloy will comprise a nickel titanium based alloy (i.e., Nitinol™), which may include additional elements which affect the characteristics of the prosthesis, such as the temperature at which the shape transformation occurs. For example, the alloy may incorporate additional metallic elements, such as copper, cobalt, vanadium, chromium, iron or the like.

It should be noted that the stents 370 described above and shown in FIGS. 17 and 22 are only representative of the lumenal prostheses that may be used with the present invention. The present invention may incorporate a variety of representative conventional stent structures made from metallic tubular materials that are currently marketed as implants for coronary, peripheral, biliary and other vessels including the Palmaz-Schatz™ balloon expandable stent, manufactured by Johnson and Johnson Interventional Systems, Co. and the Memotherm™ stent manufactured by Angiomed, a division of C.R. Bard, Inc. Other stent or graft designs that can be incorporated into the present invention include a coiled structure, such as that described in U.S. Pat. No. 5,476,505 to Limon, an open mesh or weave stent structure formed of helically wound and/or braided strands or filaments of a resilient material, described in U.S. Pat. No. 5,201,757 to Heyn, a filament knitted into a mesh cylinder, described in U.S. Pat. No. 5,234,457 to Andersen, a tubular structure having diamond shaped openings, described in U.S. Pat. Nos. 5,242,399 to Lau or U.S. Pat. No. 5,382,261 to Palmaz, Z-shaped stents as described in U.S. Pat. No. 5,282,824 to Gianturco, continuous wire stents, such as the one described in U.S. Pat. No. 5,292,331 to Boneau, stents formed of filaments that are wound into spiral or other suitable shapes as described in U.S. Pat. No. 5,314,471 to Fountaine, a continuous helix of zig-zag wire and loops described in U.S. Pat. No. 5,405,377 to Cragg and a variety of other types of stents.

What is claimed is:

1. A method of revascularizing a portion of a patient's myocardium comprising:
   positioning an active electrode in close proximity to a target site on a wall of the patient's heart wherein the active electrode comprises an electrode array including a plurality of isolated electrode terminals;
   contacting the active electrode with an electrically conducting fluid disposed in a space between the active electrode and the target site;
   inducing discharge of energetic electrons and photons from the conducting fluid by applying a sufficient high-frequency voltage between the active electrode and a return electrode; and
   directing the energetic electrons and photons to ablate tissue at the heart wall to form a revascularizing channel through at least a portion of the heart wall.

2. The method of claim 1, further comprising axially translating the active electrode surface through the portion of the heart wall to form the revascularizing channel.

3. The method of claim 1, further comprising:
   introducing at least a distal end of an electrosurgical catheter into the ventricle of the heart; and
   positioning the distal end of the catheter in close proximity to the endocardium.

4. The method of claim 1, further comprising:
   introducing at least a distal end of an electrosurgical probe through an opening in the patient's chest cavity; and
   positioning the distal end of the probe in close proximity to the epicardium.

5. The method of claim 4, wherein the probe is introduced through an intercostal penetration in the patient.

6. The method of claim 1, wherein the voltage is applied continuously between the active and return electrodes.

7. The method of claim 1, wherein the voltage is applied in pulses to correspond to beating of the patient's heart.

8. The method of claim 1, wherein the active electrode comprises a single electrode protruding from a distal end of an electrosurgical probe.

9. The method of claim 1, further including independently controlling current flow from at least two of the electrode terminals based on impedance between the electrode terminal and the return electrode.

10. The method of claim 1, further comprising forming a revascularizing channel with a lateral dimension of about 1.5 to 3.0 mm.

11. The method of claim 1, further comprising positioning a radially expandable lumenal prosthesis in the revascularizing channel to maintain patency of the channel.

12. The method of claim 1, wherein the channel formed by the active electrode surface is curved.

13. The method of claim 12, wherein the channel formed by the active electrode surface has first and second openings on one side of the heart wall, and a substantially U-shape therebetween.

14. The method of claim 1, wherein the electrode terminals are embedded in an insulating matrix to electrically isolate each terminal, the insulating matrix comprising an inorganic material.

15. The method of claim 1, wherein the plurality of return electrodes are proximally recessed from the active electrode terminals.

16. The method of claim 1, wherein the return electrode and the active electrode terminals are disposed on a distal surface of an electrosurgical probe.

17. The method of claim 1, further comprising controlling the depth of the revascularizing channel.

18. The method of claim 17, further comprising visually marking the target site on the heart wall.

19. The method of claim 17, further comprising determining a thickness of the heart wall at the target site.

20. The method of claim 17, further comprising setting a predetermined distance through the heart wall at the target site and interrupting the flow of voltage to the active electrode surface when said active electrode surface has advanced the predetermined distance to control the depth of the channel.

21. The method of claim 19, wherein the determining step comprises measuring tissue impedance beyond the distal end of the active electrode surface.

22. The method of claim 1, further comprising the step of determining when the active electrode surface has substantially penetrated through the heart wall.

23. The method of claim 22, further comprising terminating the high frequency voltage before the active electrode surface pierces an opposite wall surface of the heart wall.

24. The method of claim 1, wherein the active electrode is axially translated through at least a portion of the heart wall at a substantially constant rate.

25. The method of claim 1, wherein the electrically conductive fluid provides a conductive pathway between the active electrode and the return electrode.

26. The method of claim 1, wherein the electrically conductive fluid is isotonic saline.

27. The method of claim 1, wherein the channel is formed by a volumetric removal of the target tissue.

28. The method of claim 1, wherein the applied high-frequency voltage comprises a peak-to-peak voltage between 40 to 4000 volts.

29. The method of claim 1, wherein the applied high-frequency voltage comprises a peak-to-peak voltage between 100 to 3200 volts.

30. The method of claim 1, wherein the applied high-frequency voltage comprises a peak-to-peak voltage between 300 to 2400 volts.

31. A method of revascularizing a portion of a patient's myocardium comprising:
   positioning an active electrode in close proximity to a target site on a wall of the patient's heart, wherein the active electrode comprises an electrode array including a plurality of isolated electrode terminals;
   directing an electrically conducting fluid in a space between the active electrode and the target site; and
   applying high-frequency voltage between the active electrode and a return electrode to ablate tissue at the heart wall to form a revascularizing channel through at least a portion of the heart wall.

* * * * *